US008992469B2

(12) United States Patent
Bartlett, II et al.

(10) Patent No.: US 8,992,469 B2
(45) Date of Patent: Mar. 31, 2015

(54) RECONSTITUTION DEVICE

(71) Applicant: Glucago, LLC, El Segundo, CA (US)

(72) Inventors: Rush L. Bartlett, II, Palo Alto, CA (US); Peter M. Greco, Jr., Hermosa Beach, CA (US); Barry J. Davignon, Terre Haute, IN (US)

(73) Assignee: Glucago LLC, El Segundo, CA (US)

( * ) Notice: Subject to any disclaimer, the term of this patent is extended or adjusted under 35 U.S.C. 154(b) by 0 days.

(21) Appl. No.: 14/097,890

(22) Filed: Dec. 5, 2013

(65) Prior Publication Data

US 2014/0228746 A1  Aug. 14, 2014

Related U.S. Application Data

(63) Continuation of application No. PCT/US2013/047935, filed on Jun. 26, 2013.

(60) Provisional application No. 61/664,255, filed on Jun. 26, 2012, provisional application No. 61/763,651, filed on Feb. 12, 2013, provisional application No. 61/839,142, filed on Jun. 25, 2013.

(51) Int. Cl.
*A61M 37/00* (2006.01)
*A61M 5/315* (2006.01)
*A61J 1/20* (2006.01)

(52) U.S. Cl.
CPC .......... *A61M 5/31596* (2013.01); *A61J 1/2093* (2013.01)
USPC .............................................. 604/90; 604/91

(58) Field of Classification Search
CPC . A61M 5/284; A61M 5/285; A61M 5/31596; A61M 5/31513; A61M 5/315; A61J 1/20; A61J 1/2093; A61J 1/2096
USPC ....................................................... 604/82–91
See application file for complete search history.

(56) References Cited

U.S. PATENT DOCUMENTS 2,591,706 A * 4/1952 Lockhart .......................... 604/90
2,869,543 A   1/1959 Ratcliff et al.
(Continued)

FOREIGN PATENT DOCUMENTS

DE  1291859   4/1969
EP  0112574   7/1984
(Continued)

OTHER PUBLICATIONS

Oct. 22, 2013 International Search Report for PCT/US2013/038490 issued by the European Patent Office as Searching Authority, Oct. 22, 2013 pp. 1-7.

(Continued)

*Primary Examiner* — Quynh-Nhu H Vu
(74) *Attorney, Agent, or Firm* — Dorsey & Whitney LLP

(57) ABSTRACT

An apparatus comprises a plunger able to fit in a cartridge or syringe. The plunger includes an outer portion and a deflection portion. The outer portion is able to engage the body of the cartridge or syringe. The outer portion is operable to apply a first radial force to the cartridge or syringe. The deflection portion is positioned within the outer portion and is movable between a locked position and an unlocked position. The deflection portion in the unlocked position causes the outer portion to apply a second radial force to the cartridge or syringe.

13 Claims, 38 Drawing Sheets

(56) References Cited

U.S. PATENT DOCUMENTS

| | | | |
|---|---|---|---|
| 3,678,931 A * | 7/1972 | Cohen | 604/90 |
| 3,699,961 A * | 10/1972 | Szpur | 604/89 |
| 3,785,379 A * | 1/1974 | Cohen | 604/88 |
| 3,838,689 A * | 10/1974 | Cohen | 604/90 |
| 3,885,710 A | 5/1975 | Cohen | |
| 3,939,833 A * | 2/1976 | Hansson et al. | 604/202 |
| 4,059,109 A | 11/1977 | Tischlinger | |
| 4,061,144 A | 12/1977 | Strickman et al. | |
| 4,215,701 A | 8/1980 | Raitto | |
| 4,715,854 A | 12/1987 | Vaillancourt | |
| 4,921,491 A | 5/1990 | Champ | |
| 5,279,606 A * | 1/1994 | Haber et al. | 604/403 |
| 5,352,196 A | 10/1994 | Haber et al. | |
| 5,377,689 A * | 1/1995 | Mercereau | 600/576 |
| 5,433,705 A | 7/1995 | Giebel et al. | |
| 5,562,631 A | 10/1996 | Bogert | |
| 5,620,423 A | 4/1997 | Eykmann et al. | |
| 5,630,796 A | 5/1997 | Bellhouse et al. | |
| 5,779,668 A | 7/1998 | Grabenkort | |
| 5,785,683 A * | 7/1998 | Szapiro et al. | 604/89 |
| 5,971,953 A | 10/1999 | Bachynsky | |
| 6,001,080 A | 12/1999 | Kuracina et al. | |
| 6,001,089 A | 12/1999 | Burroughs et al. | |
| 6,602,223 B2 * | 8/2003 | Szapiro et al. | 604/89 |
| 2003/0100921 A1 | 5/2003 | Addis et al. | |
| 2004/0186432 A1 | 9/2004 | Barry et al. | |
| 2006/0178638 A1 | 8/2006 | Reynolds | |
| 2008/0234654 A1 | 9/2008 | McCarthy et al. | |
| 2008/0319400 A1 * | 12/2008 | Thorne et al. | 604/191 |
| 2009/0036864 A1 | 2/2009 | Moy et al. | |
| 2009/0247957 A1 | 10/2009 | Heutschi | |
| 2009/0254035 A1 | 10/2009 | Kohlbrenner et al. | |
| 2010/0168712 A1 | 7/2010 | Tuckwell et al. | |
| 2011/0106021 A1 | 5/2011 | Ruegg et al. | |
| 2013/0226081 A1 | 8/2013 | Davies et al. | |

FOREIGN PATENT DOCUMENTS

| | | |
|---|---|---|
| EP | 0340899 A2 | 11/1989 |
| EP | 0511402 A1 | 11/1992 |
| JP | 09-225032 | 9/1997 |
| WO | 2007131013 A1 | 11/2007 |

OTHER PUBLICATIONS

Oct. 8, 2013 International Search Report for PCT/US2013/047935 issued by the Korean Patent Office as Searching Authority, Oct. 8, 2013 pp. 1-3.

Oct. 8, 2013 Written Opinion for PCT/US2013/047935 issued by the Korean Patent Office as Searching Authority, Oct. 8, 2013, pp. 1-8.

Mar. 19, 2013 International Search Report for PCT/US2012/056318 issued by the Korean Patent Office as Search Authority, Mar. 19, 2013 pp. 1-3.

Jun. 9, 2011 International Search Report for PCT/US2011/030910 issued by the United States Patent Office as Search Authority, Jun. 9, 2011 pp. 1-2.

* cited by examiner

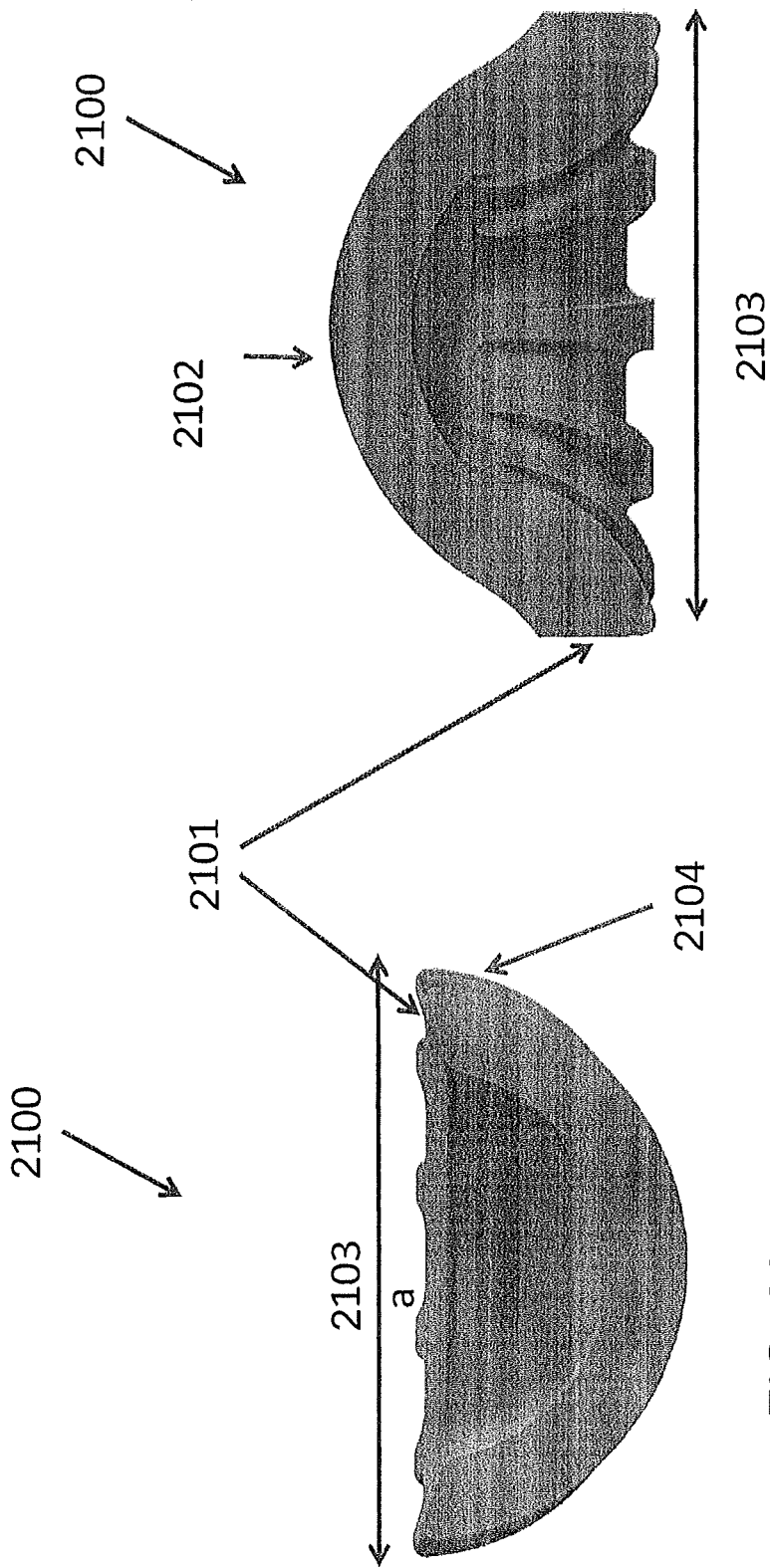

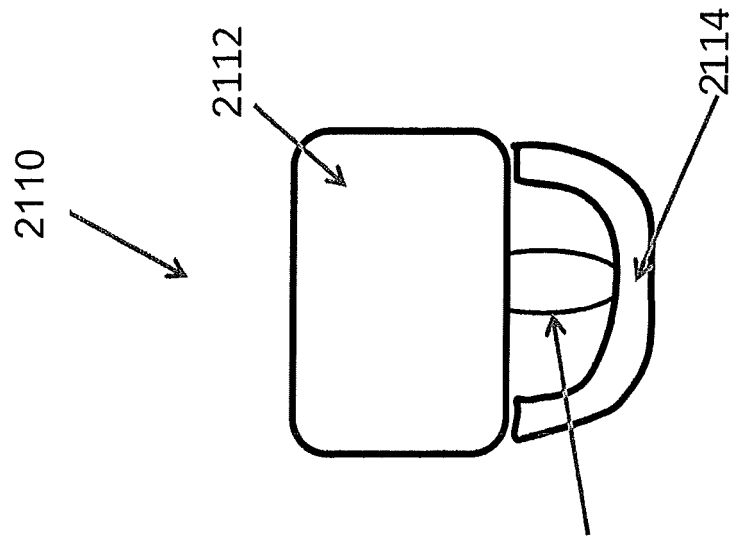
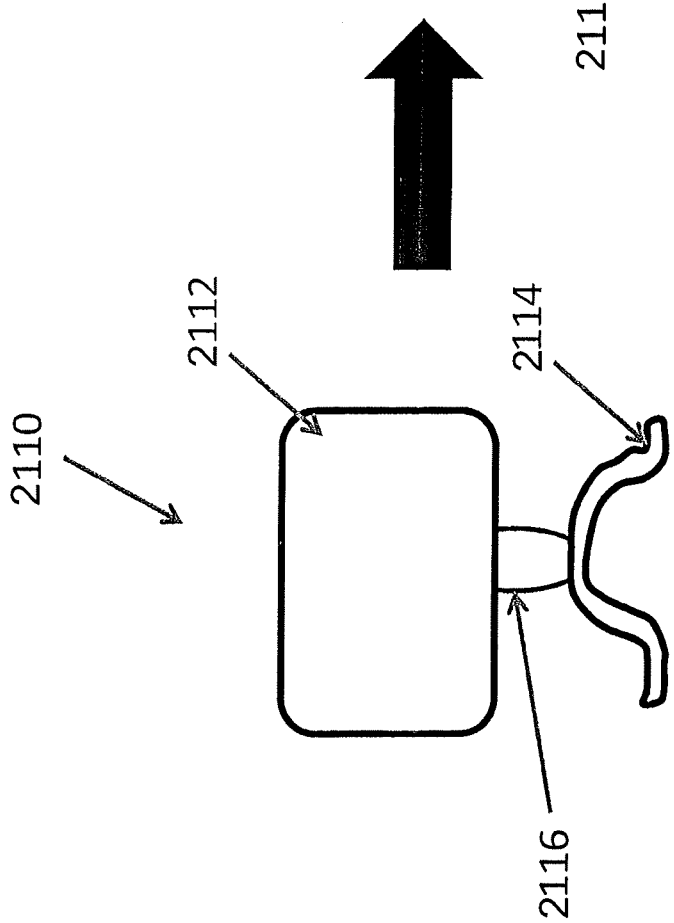
FIG. 23A
FIG. 23B

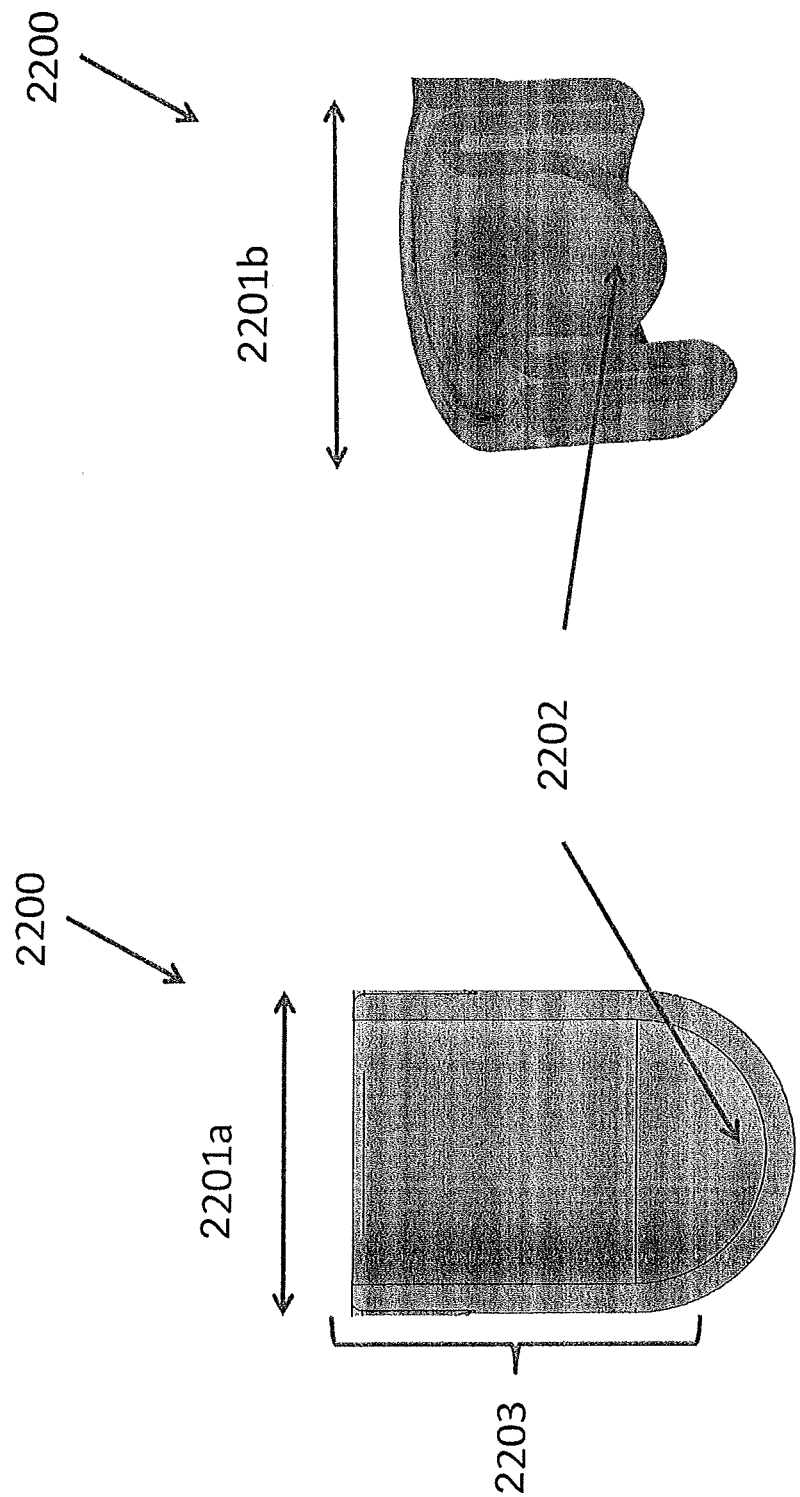

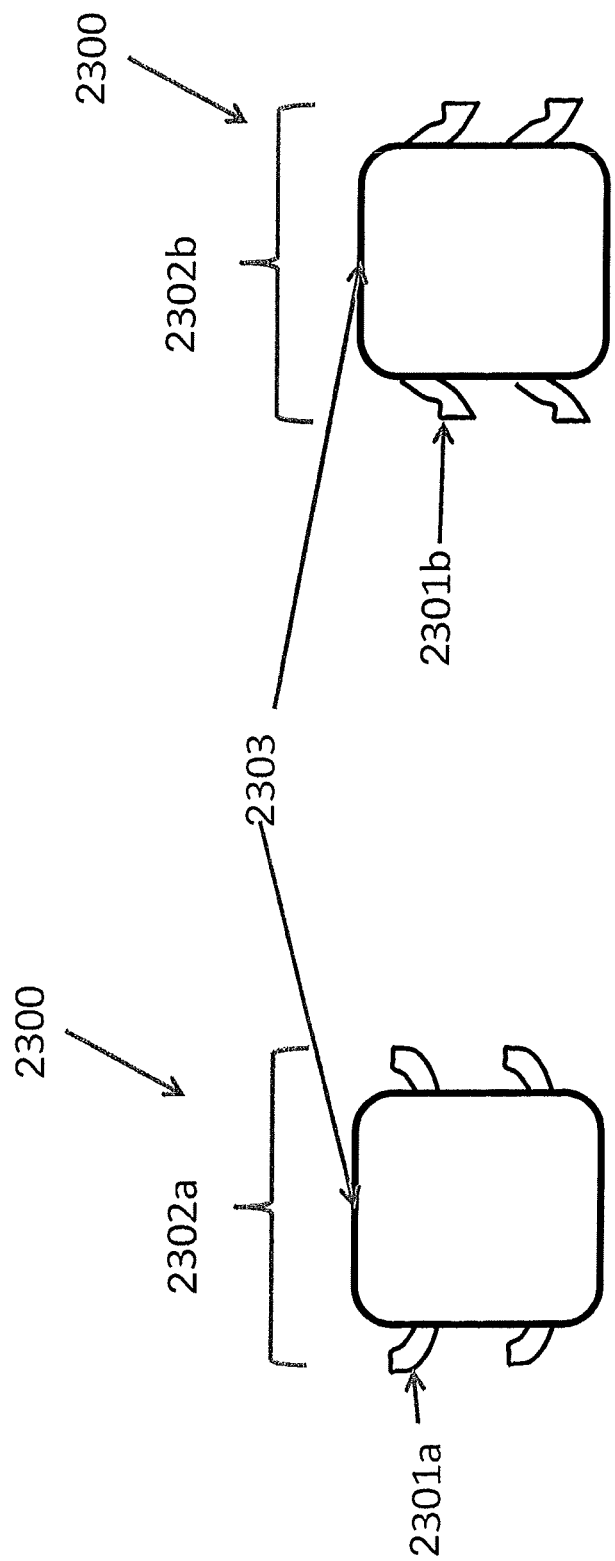

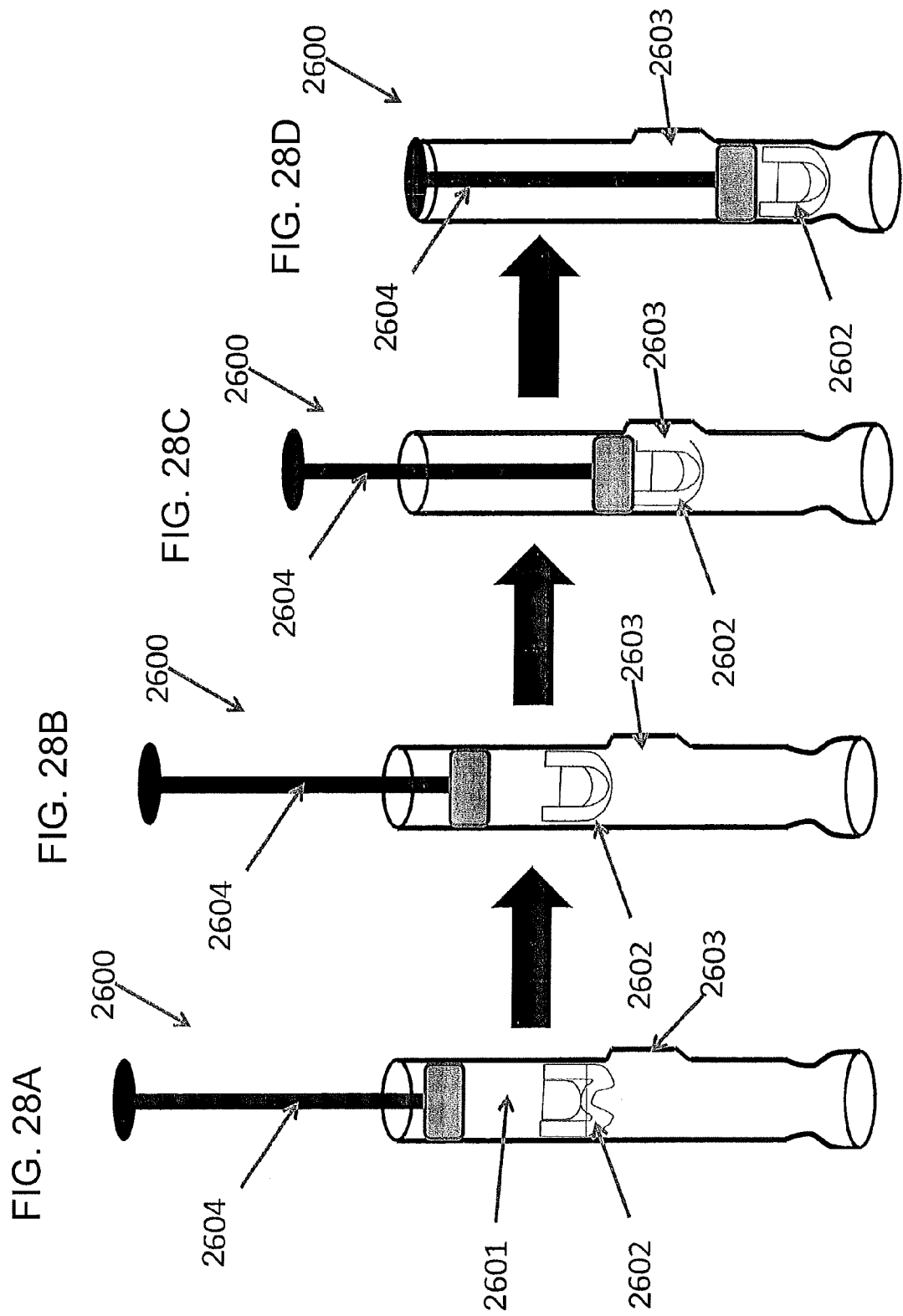

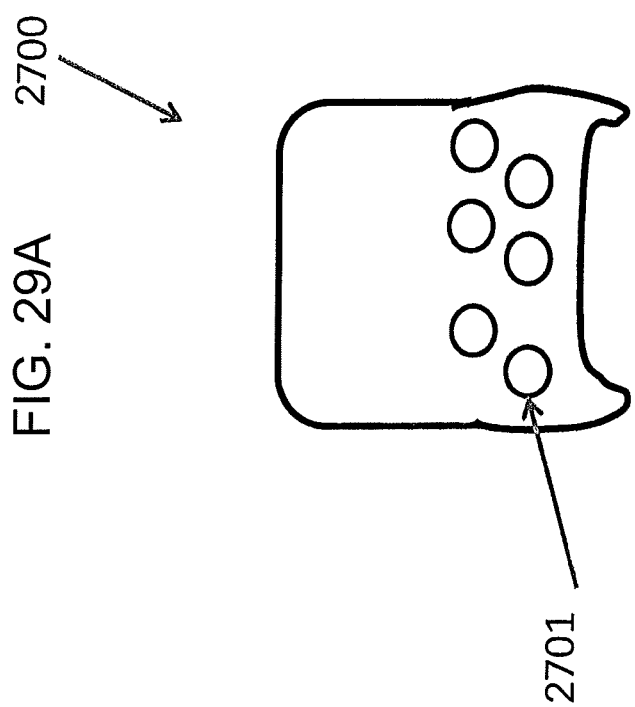
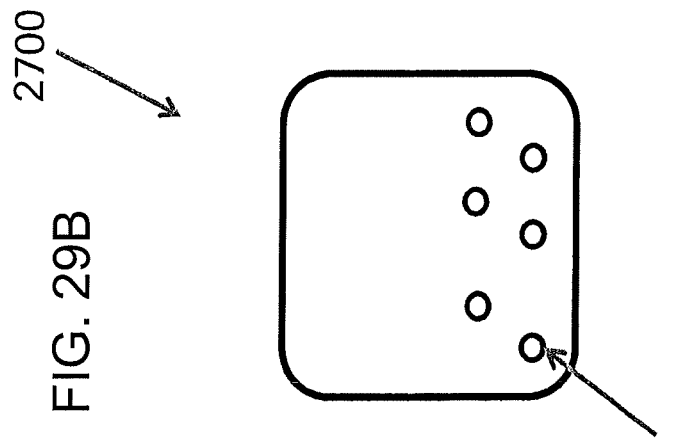
FIG. 29A
FIG. 29B

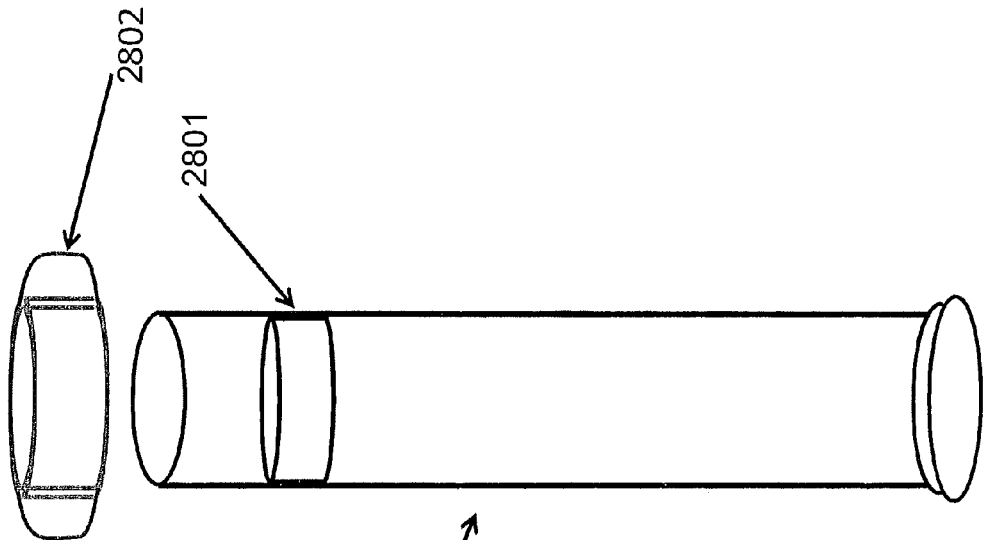
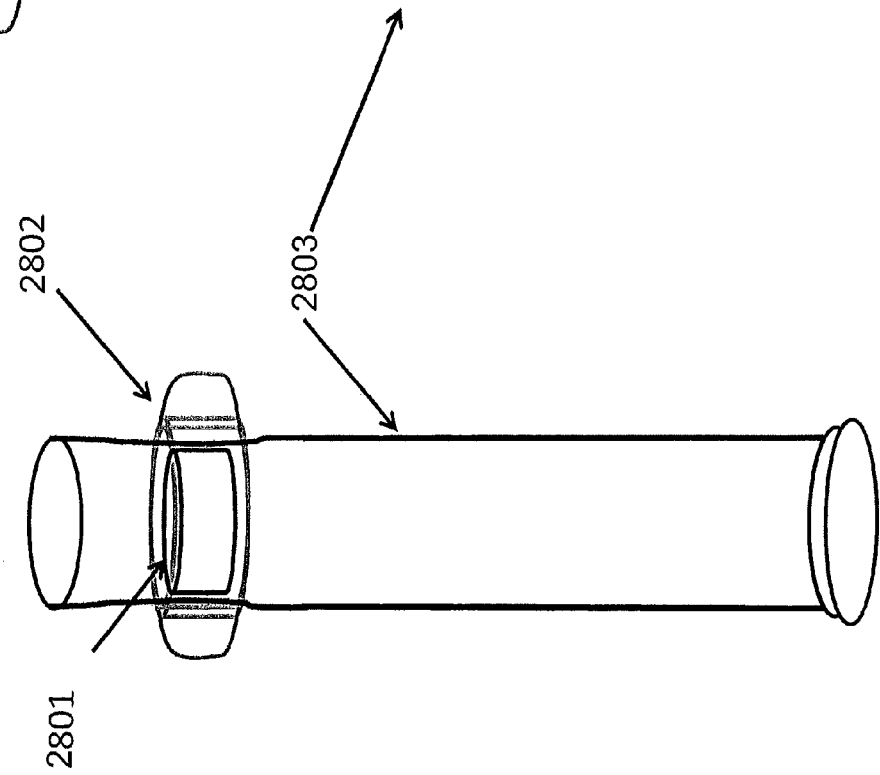

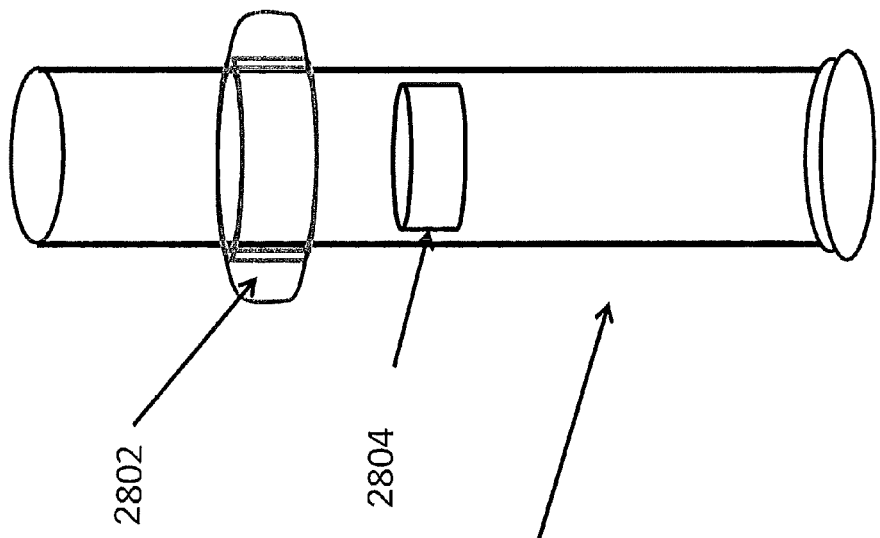
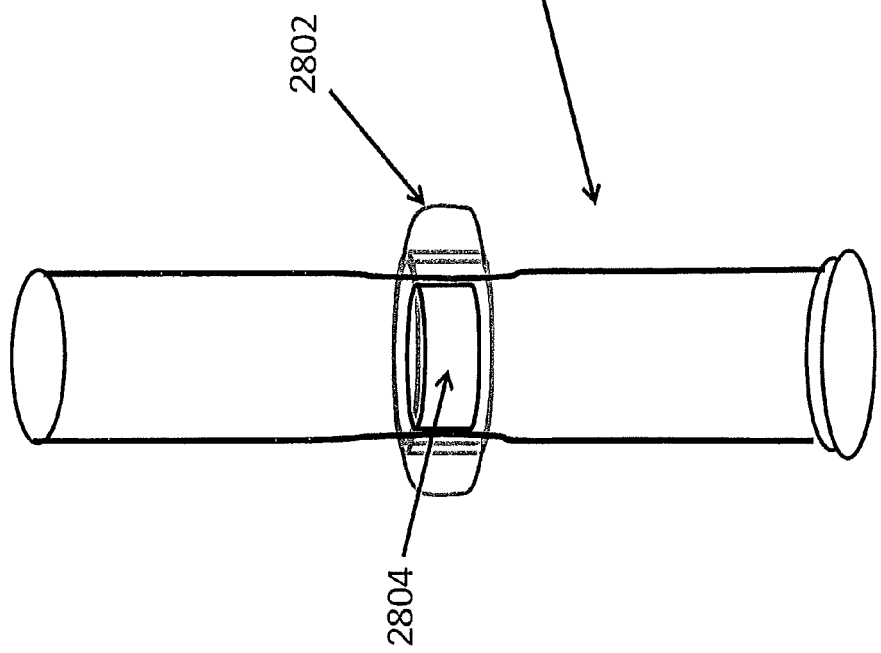

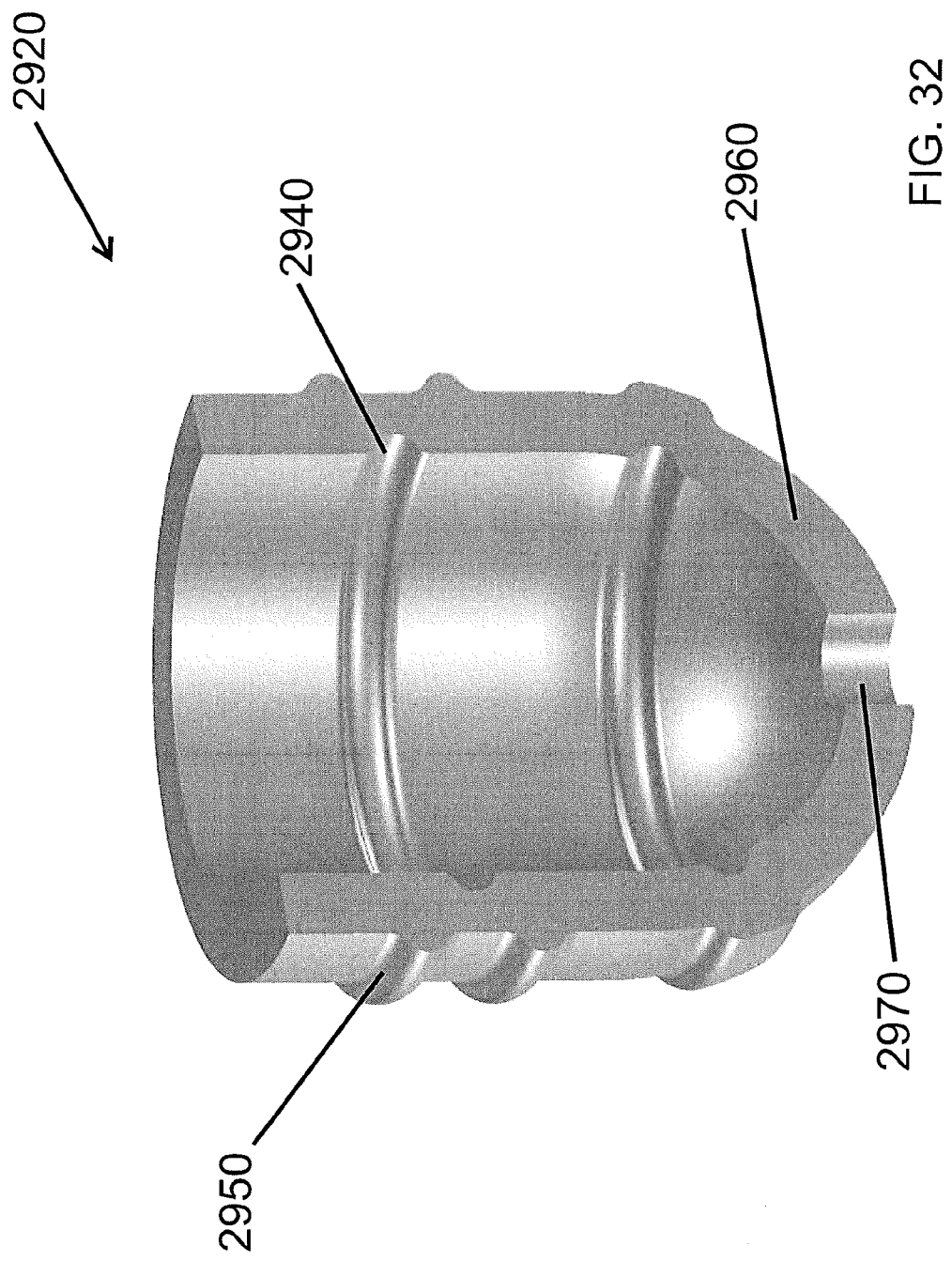

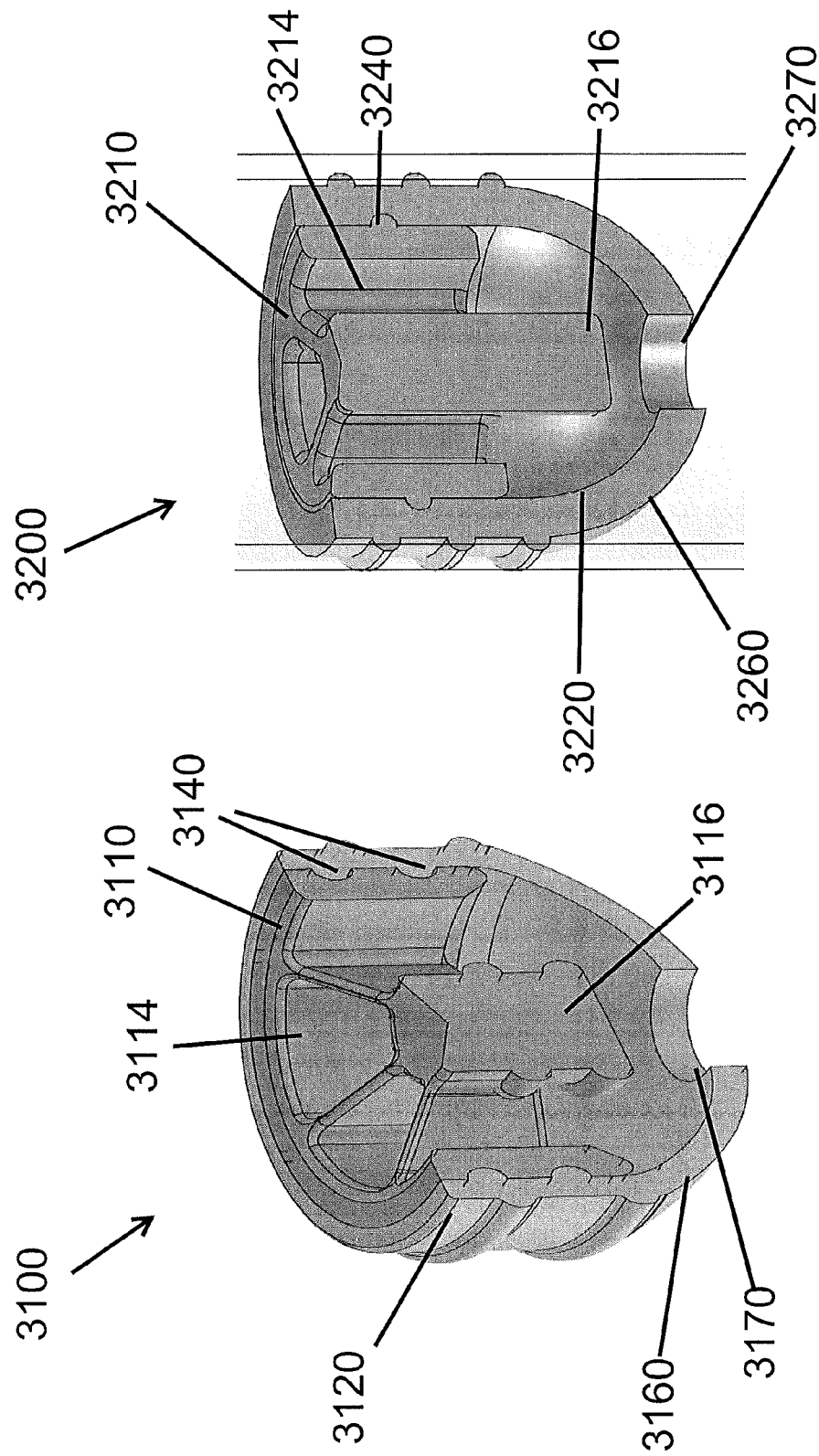

RECONSTITUTION DEVICE

CROSS-REFERENCE TO RELATED APPLICATIONS

This application is a continuation application of PCT Serial No. PCT/US2013/047935, filed Jun. 26, 2013, which claims priority to U.S. Provisional Patent Application No. 61/664,255, filed on Jun. 26, 2012; U.S. Provisional Patent Application No. 61/763,651, filed on Feb. 12, 2013; and U.S. Provisional Patent Application No. 61/839,142, filed on Jun. 25, 2013. The disclosures of all the above-referenced patent applications are hereby fully incorporated by reference.

BACKGROUND

Many drugs must be stored independent of another substance (another drug or a diluent) and then mixed together in order to be administered to the patient. This administration could take place through the oral, intravenous, intradermal, intramuscular, subcutaneous, mucus membrane, skin contacting, or inhalation routes to enter the body, although this is not an exhaustive list. These medications may comprise a combination of a solid and a liquid, or a liquid with another liquid. These solid drugs mixed with a liquid or liquid drugs mixed with another liquid are used to treat in a variety of applications including but not limited to vaccination, diagnostic agents, therapeutics, pharmaceuticals, controlled release formulations, polymer drug conjugates, liposomes, gene therapy agents, DNA, RNA, proteins, peptides, small molecules, large molecules, and many others.

Currently there are only a few methods of administration that facilitate this mixing process of the solid and liquid or the liquid and liquid. The main device categories include: needle spikes, needless adaptors, three way valves, glass syringes with a bypass built into the glass, and more complex devices that facilitate medication transfer between two separate containers. The devices currently on the market either are difficult to use but low cost or alternatively are high cost and easier to use.

While a variety of reconstitution devices have been made and used, it is believed that no one prior to the inventor(s) has made or used an invention as described herein.

BRIEF SUMMARY OF THE INVENTION

The disclosure herein describes a plunger for use in a container or syringe that is operable to maintain high friction when a strong seal is desired, such as during storage or transport, while allowing the friction force to decrease when desired to facilitate an acceptable glide force during administration and or mixing of components within the container. Such mixing may occur during a reconstitution process or any other suitable process. The plunger and/or stopper may be locked or fixed in place with a strong force until the user unlocks and reduces the fixation force during use. Once unlocked, the glide force between the plunger and the container holding the plunger is decreased, thereby promoting advancement of the plunger within the container. This "locking plunger" has many applications in several different embodiments including but not limited to: syringes, pre-filled syringes, cartridges, dual or multi-chamber delivery devices, and vials. The locking feature of the exemplary plunger described herein is achieved in some versions by the dynamic shape shifting of the plunger. The plunger, which may be constructed of rubber or any other suitable elastomeric material, comes out of the mold in a specific shape with a specific diameter and is biased to maintain that shape and diameter. The shape may be specifically designed to be dynamic in that the plunger can be flipped, expanded, contracted, squished, compressed, or rolled into a different position which causes it to alter its dimensions, expand or increase its diameter, or any other means to increase the force that it exerts on the container walls and thus the glide friction and seal. In other words, the plunger may be inverted to cause it to exert increased outward force that may translate into outward force applied to the wall of a container it is being held in. This increased force and resulting friction is maintained while the plunger or stopper is in its "locked" or altered/inverted position. When a predetermined amount of pressure and or vacuum is applied to one end of the plunger or an external component, it causes the plunger to dynamically shift to another shape and the force exerted on the container walls decreases to facilitate desired glide force for use. When force is applied to "unlock" the plunger or stopper, the force that the plunger exerts on the container walls will increase until it reaches a breaking point at which point the force/friction will decrease to the predetermined desired measurement. It will be appreciated that some versions may include this physical response to increased force and some may not.

This unlocking may be desirable for single or multi chambered systems that change pressure during operation. In the case of a dual chambered system for a lyophilized component, the solid component may be stored under partial or full vacuum. This vacuum creates a pulling force on a middle stopper or plunger operable to urge the middle stopper to creep down into a bypass region. To account for this vacuum, the friction on the wall must be greater than the vacuum pulling force to keep the stopper or plunger in the center of the chamber. Once the dual chambered system is activated, the liquid chamber, which is commonly at atmospheric or a higher pressure, mixes with the solid component stored under the partial vacuum by flowing through a bypass or flow channel. In this scenario after the pressure in the two chambers equalize, the effective force required to push the center stopper or plunger is now greatly increased since there is no pulling force remaining from the difference in pressure between the two chambers. It will be appreciated that this may create the potential scenario where the middle stopper or plunger is too difficult to move for use with some medical applications, especially ones that require large volumes and or large diameters for the vials, cartridges, or syringes. The locking stopper described herein will maintain a strong seal and high wall friction until the stopper is activated. Once activated and advanced forward, this reduction in the wall friction will allow for easier movement in single or multi chambered systems at varying or same pressures. If a dual chamber system with different pressures in the chambers is desired, when the stopper reaches the bypass region and the pressure equalizes between the multiple chambers, this reduction of wall friction for movement will allow the stopper to be moved at a lower force than what would have been required if the stopper had the same wall friction as it did in the storage state.

The disclosed device will facilitate the storage of two substances independent of each other and upon activation, introduce the two creating a solution. This device will then facilitate the dispensing of the resulting solution. The device can and will be used both for solid (lyophilized, spray dried or other) drugs to be mixed with a liquid, or two liquids (one or both being drugs). The disclosed device could be used with lyophilized materials and a diluent but the device disclosed will also facilitate mixing of two liquids, a spray dried compound and a liquid, a precipitated solid and a liquid, a semi solid or colloid and a liquid, or any combination of a liquid and any other substance as would be apparent to one of ordinary skill in the art in view of the teachings herein. Also, it should be noted that multiple disclosed containers with reconstitution components could be attached or added together to facilitate mixing of more than two components. Additional configurations containing more than two separate compartments, vials, chambers, or containers will be apparent to one of ordinary skill in the art in view of the teachings herein.

Currently disclosed are two merely exemplary devices having separation components that allow for flow through the components to facilitate mixing upon activation by some outside force. This outside force causes a component to fully or partially invert which would facilitate the formation of a flow path through various embodiments. This flow path would enact the ability of the device to reconstitute materials. More specifically this valve could be a one piece pressure valve which shrinks its external diameter upon activation by a force to cause a full or slight inversion or flipping of the device. This force could include pressure, gravity, or outside mechanical intervention or movement by a person or device or any other suitable force as would be apparent to one of ordinary skill in the art in view of the teachings herein.

These and other aspects and embodiments will be described in further detail below, in reference to the attached drawing figures.

BRIEF DESCRIPTION OF DRAWINGS

It is believed the present invention will be better understood from the following description of certain examples taken in conjunction with the accompanying drawings, in which like reference numerals identify the same elements and in which:

FIG. 22A depicts a side, cross sectional view of an exemplary stopper in an unlocked state;

FIG. 22B depicts a side, cross sectional view of the stopper of FIG. 22A in a locked state;

FIG. 23A depicts a side elevation view of an exemplary alternative stopper in a locked state;

FIG. 23B depicts a side, elevation view of the stopper of FIG. 23A in an unlocked state;

FIG. 24A depicts a side, cross sectional view of an exemplary alternative stopper in an unlocked state;

FIG. 24B depicts a perspective, cross sectional view of the stopper of FIG. 24A in a locked state;

FIG. 25A depicts a side, elevation view of an exemplary alternative stopper with a plurality of side flanges with the stopper in an unlocked state;

FIG. 25B depicts a side, elevation view of the stopper of FIG. 25A in a locked state;

FIG. 28A depicts a side, cross sectional view of an exemplary alternative stopper inserted into a dual chambered syringe with the stopper in a locked position;

FIG. 28B depicts a side, cross sectional view of the stopper and syringe of FIG. 28A with the stopper in an unlocked position;

FIG. 28C depicts a side, cross sectional view of the stopper and syringe of FIG. 28A with the stopper drawn forward in part due to a vacuum in the lower chamber;

FIG. 28D depicts a side, cross sectional view of the stopper and syringe of FIG. 6A with the stopper further advanced by user advancement of a push rod;

FIG. 29A depicts a side, cross sectional view of an exemplary alternative version of a stopper with dynamic cells in an expanded position;

FIG. 29B depicts a side, cross sectional view of the stopper of FIG. 29A with the cells in a compressed position;

FIG. 30A depicts a side, transparent view of an exemplary alternative stopper with a sleeve around a housing;

FIG. 30B depicts a side, transparent view of the stopper of FIG. 30A with the sleeve removed;

FIG. 30C depicts a side, transparent view an exemplary alternative stopper with ridges with a sleeve around a housing;

FIG. 30D depicts a side, transparent view of the stopper of FIG. 30C with the sleeve removed from the housing;

FIG. 32 depicts a side, cross sectional, perspective view of a first plunger portion of the plunger of FIG. 31;

FIG. 36 depicts a side, cross sectional, perspective view of an exemplary alternative plunger with a multiple ribbed plug;

FIG. 37 depicts a side, cross sectional, perspective view of an exemplary alternative plunger with a straight, cylindrical plug;

Figure 1A:
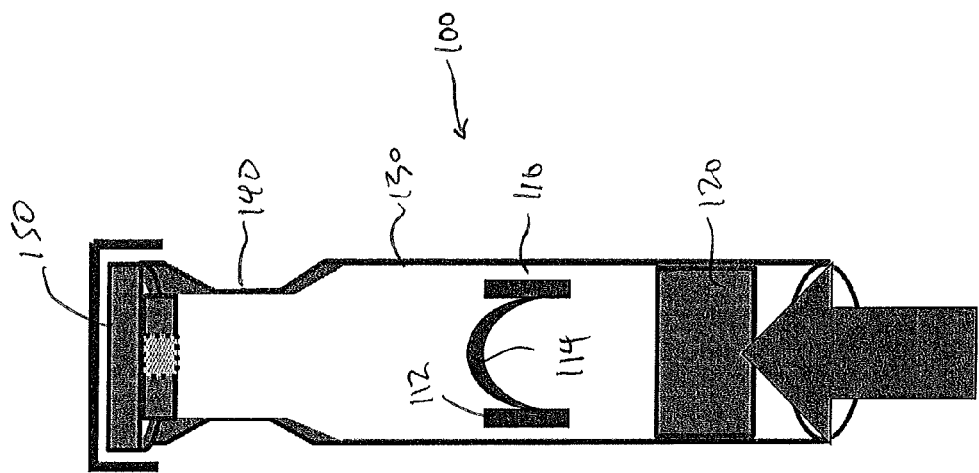
FIG. 1A depicts a cross sectional elevation view of an exemplary reconstitution device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

An exemplary reconstitution device, which will be described in further detail below, will be operable for use with, for instance, syringe or cartridge devices. Reconstitution device may be constructed to fit in a conventional syringe, or in other instances reconstitution device may be used with a syringe designed for use with reconstitution device. Indeed, any suitable device for reconstituting a fluid may be used with reconstitution device as would be apparent to one of ordinary skill in the art in view of the teachings herein.

Figure 1B:
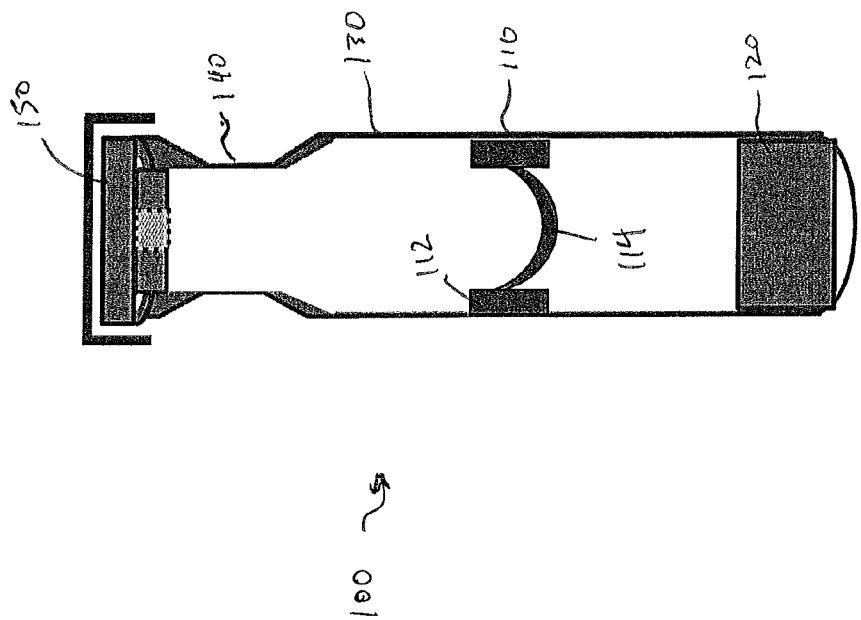
FIG. 1B depicts a cross sectional elevation view of an exemplary reconstitution device with a plunger stopper advancing.

FIGS. 1A-1B shows an exemplary reconstitution device (100) comprising a cartridge body (130). At one end of cartridge body (130) is an end stopper (150) and at the other end is a plunger stopper (120). Cartridge body (130) is able to hold, for instance, two components for mixing such a lyophilized component and a liquid operable to reconstitute the lyophilized component. Cartridge body (130) of the illustrated version has a cylindrical shape with a neck portion (140) having a narrower diameter than cartridge body (130), but it will be appreciated that in other versions, cartridge body (130) may have any suitable shape as would be apparent to one of ordinary skill in the art in view of the teachings herein. Plunger stopper (120) may be urged longitudinally along cartridge body (130) to help facilitate reconstitution, such as shown in FIG. 1B. End stopper (150) may simply block an end of cartridge body (130) such that fluid does not escape. In other instances, end stopper (150) may include an opening to urge a fluid therefrom. Other suitable configurations will be apparent to one of ordinary skill in the art in view of the teachings herein.

FIG. 1A-1B also shows an exemplary reactive stopper (110). Reactive stopper (110) comprises contact portion (112) and moveable portion (114). In the exemplary version, reactive stopper (110) comprises a rubber or silicon material, but any other suitable material may be used as would be apparent to one of ordinary skill in the art. Furthermore, in the illustrated version, reactive stopper (110) has a generally circular shape to complement the cylindrical shape of cartridge body (130). Other suitable shapes for reactive stopper (110) may be used as would be apparent to one of ordinary skill in the art in view of the teachings herein. Contact portion (112) is operable to press outwardly against the walls of cartridge body (130) as shown for instance in FIG. 1A. As a result, reactive stopper (110) forms a fluid tight seal with the wall of cartridge body (130). It will be appreciated that movable portion (114) may be movable between a first position shown in FIG. 1A and a second position shown in FIG. 1B. It will be appreciated that in first position shown in FIG. 1A, as pressure is applied from the direction of plunger stopper (120) toward reactive stopper (110), reactive stopper (110) applies more pressure against the walls of cartridge body (130). In other words, reactive stopper (110) is operable to translate at least a portion of longitudinally applied pressure into outwardly directed pressure against the walls of cartridge body (130).

Figure 2B:
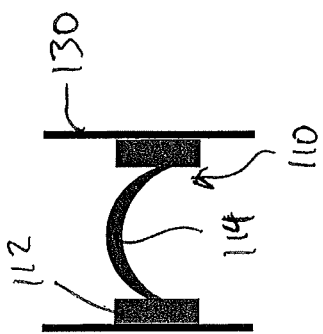
FIG. 2B depicts a cross sectional elevation view of the reactive stopper of FIG. 1A with the movable portion actuated.
Figure 2A:
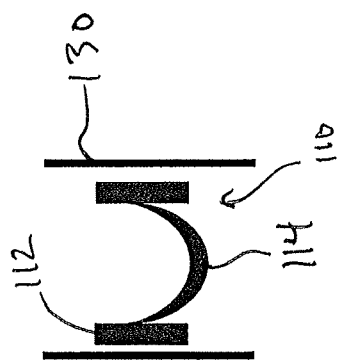
FIG. 2A depicts a cross sectional elevation view of the reactive stopper of FIG. 1A.

It will be appreciated that once a sufficient amount of pressure is applied through plunger stopper (120) to reactive stopper (110) through a fluid contained there between, moveable portion (114) moves to the position shown in FIG. 1B. It will further be appreciated that once reactive stopper (110) is in the position shown in FIG. 1B, the overall radius of reactive stopper (110) decreases, thereby allowing free flowing of fluid within cartridge body (130) which facilitates reconstitution. FIGS. 2A-2B show a close up version of a portion of cartridge body (130) to illustrate reactive stopper (110). It will be appreciated that even though reactive stopper (110) in FIGS. 1A-1B show reactive stopper (110) moving in a particular direction, other movement patterns for reactive stopper (110) may be used as would be apparent to one of ordinary skill in the art in view of the teachings herein.

Figure 4:
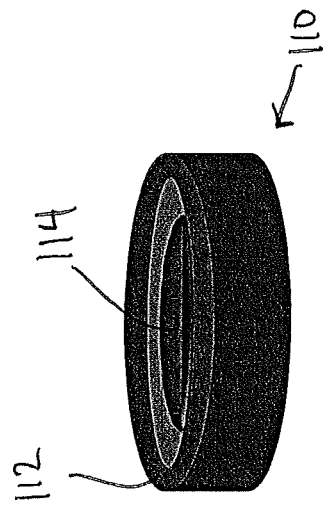
FIG. 4 depicts a perspective view of the reactive stopper of FIG. 3.
Figure 3:
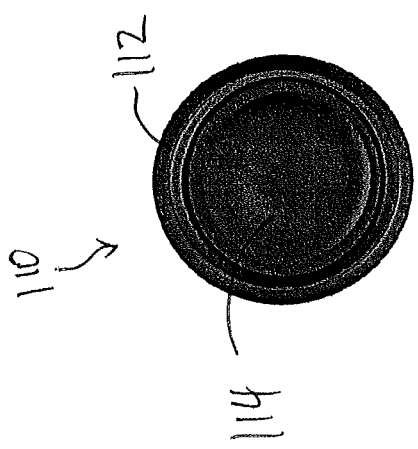
FIG. 3 depicts a top plan view of the reactive stopper of FIG. 2A.

FIG. 3 shows a top plan view of reactive stopper (110) with movable portion (114) and contact portion (112). As shown in the illustrated version, movable portion (114) and contact portion (112) joins at a ridge. FIG. 4 merely shows a perspective view of reactive stopper (110). As shown in the illustrated version, the sides of reactive stopper (110) may be cylindrical to complement and form a seal with the sides of reactive stopper (110). Other suitable shapes for reactive stopper (110) may be used as would be apparent to one of ordinary skill in the art.

Thus, in one method of using reconstitution device (100) as shown in FIGS. 1A-1B, for instance, cartridge body (130) may be filled partly with a fluid or lyophilized compound for later reconstitution. Reactive stopper (110) may be placed in to cartridge body (130) to separate the first substance placed into cartridge body (130) from, for instance, a fluid for reconstituting the first component. The entire cartridge body (130) for instance may be placed directly into a syringe body for use or cartridge body (130) may be built into a syringe. Once the user is ready to reconstitute the fluid, plunger stopper (120) may be longitudinally advanced as shown in FIG. 1B. As plunger stopper (120) is advanced, movable portion (114) flips or inverts its profile in the direction of the applied pressure from plunger stopper (120). Thereafter, the bias of reactive stopper (110) may be such that the overall diameter of reactive stopper (110) decreases as shown in FIG. 1B, which allows fluid flow throughout cartridge body (130). The user may then advance plunger stopper (120) further thereby urging reconstituted fluid from cartridge body (130) out through an opening in end stopper (150). It will be appreciated that other exemplary uses of reconstitution device (100) may be used as would be apparent to one of ordinary skill in the art in view of the teachings herein.

Figure 5A:
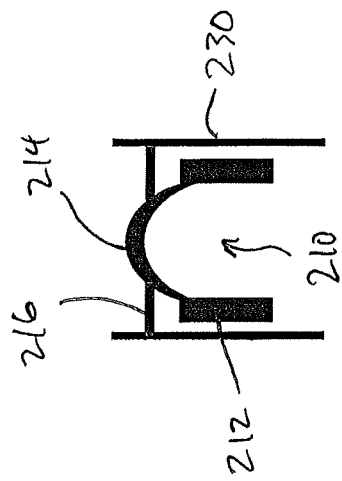
FIG. 5A depicts a cross sectional elevation view of an exemplary alternative version of a reactive stopper.
Figure 5B:
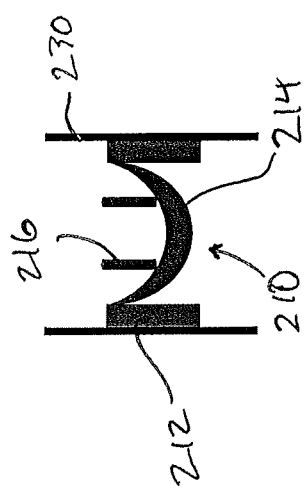
FIG. 5B depicts a cross sectional elevation view of the reactive stopper of FIG. 5A with the movable portion actuated.

FIGS. 5A-5B show a cross sectional view of an alternative cartridge body (230) with an alternative version of reactive stopper (210). Reactive stopper (210) includes contact portion (212) that is biased to provide pressure against the sides of cartridge body (230) as well as a movable portion (214). Attached to movable portion (214) is a plurality of arms or bumps (216). Arms or bumps (216) are positioned such that fluid may flow around arms or bumps (216). In the exemplary version, two arms (216) are shown, but it will be appreciated that any suitable number of arms or bumps (216) may be used as would be apparent to one of ordinary skill in the art in view of the teachings herein. Reactive stopper (210) is operable to move from a first position shown in FIG. 5A to a second position shown in FIG. 5B. When reactive stopper (210) is in the first position, reactive stopper (210) forms a fluid seal within cartridge body (230). In the second position shown in FIG. 5B, movable portion (214) flips upward and arms or bumps (216) extend radially outward against the sides of cartridge body (230). Arms or bumps (216) are operable to stabilize reactive stopper (210) once movable portion (214) and contact portion (212) decrease in diameter as seen in FIG. 5B. When arms or bumps (216) extend outward as seen in FIG. 5B, fluid is able to flow around arms or bumps (216). These arms or bumps (216) may also facilitate the collapsing of reactive stopper (210) inward or simply be used as a guide to keep reactive stopper (210) from twisting, rotating, or inverting undesirably.

Figure 6A:
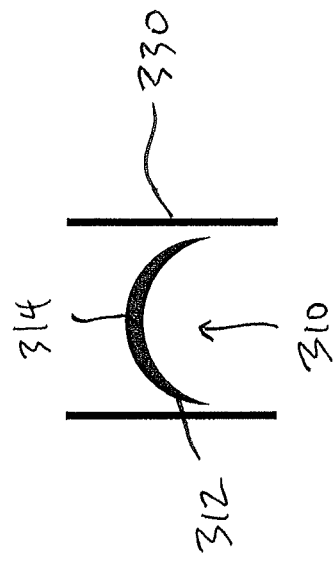
FIG. 6A depicts a cross sectional elevation view of yet another alternative exemplary version of a reactive stopper having a spherical cap shape.
Figure 6B:
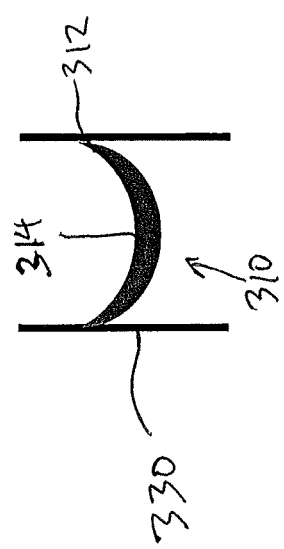
FIG. 6B depicts a cross sectional elevation view of the reactive stopper of FIG. 6A with the movable portion actuated.

FIGS. 6A-6B show another exemplary version of a reactive stopper (310) for use with a reconstitution device with a cartridge body (330). Reactive stopper (310) in the illustrated version has a generally spherical cap shape. Reactive stopper (310) has a contact portion (312) and a movable portion (314). Contact portion (312) applies an outwardly applied pressure against cartridge body (330). Movable portion (314) is operable to apply outward pressure against the walls of cartridge body (330) as a result of longitudinal pressure applied to the convex side of reactive stopper (310) in FIG. 6A. After a sufficient amount of longitudinal pressure is applied through, for instance, a plunger, movable portion (314) flips as seen in FIG. 6B, bringing contact portion (312) inward such that the overall diameter of reactive stopper (310) decreases, thereby allowing fluid to flow around reactive stopper (310).

Figure 7B:
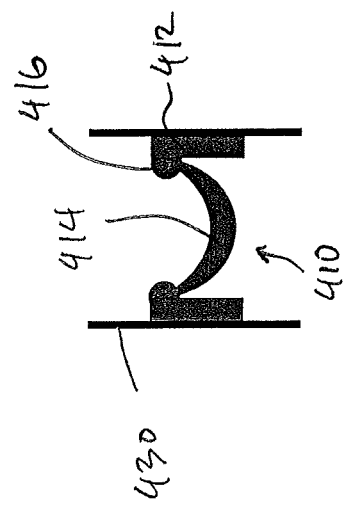
FIG. 7B depicts a cross sectional elevation view of the reactive stopper of FIG. 7A with the movable portion actuated.
Figure 7A:
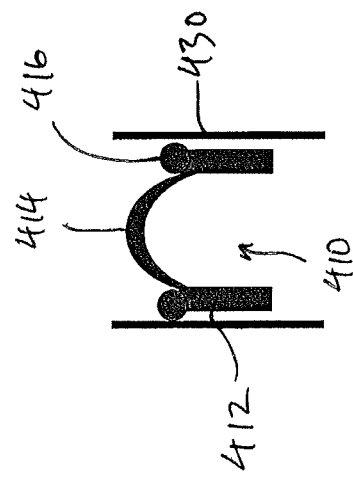
FIG. 7A depicts a cross sectional elevation view of yet another alternative exemplary version of a reactive stopper having wall bumps.

FIGS. 7A-7B show yet another exemplary version of a reactive stopper (410) within a cartridge body (430) with wall gripping features. Reactive stopper (410) shown in FIG. 7A has a ring-shaped contact portion (412) and a spherical cap-shaped movable portion (414). Reactive stopper (410) also comprises wall hugging bumps (416) positioned near the connection between movable portion (414) and contact portion (412). In the version shown in FIG. 7A, reactive stopper (410) forms a fluid seal within cartridge body (430). Upon reacting to longitudinal pressure applied to reactive stopper (410), movable portion (414) flips upward to the position shown in FIG. 7B. Bumps (416) also pivot outward to come in contact with cartridge body (430). As a result, bumps (416) grip cartridge body (430) even though contact portion (412) no longer is in contact with cartridge body (430). It will be appreciated that while the cross sectional views shown in FIGS. 7A-7B show only two bumps (416), more than two bumps (416) may be used around the circumference of reactive stopper (410). Furthermore, it will be understood that while bumps (416) are in contact with cartridge body (430), fluid may freely flow around bumps (416). Bumps (430) are operable to generally keep reactive stopper (410) stable, but it will be appreciated that other suitable uses for bumps (430) may be used as would be apparent to one of ordinary skill in the art in view of the teachings herein.

Figure 8B:
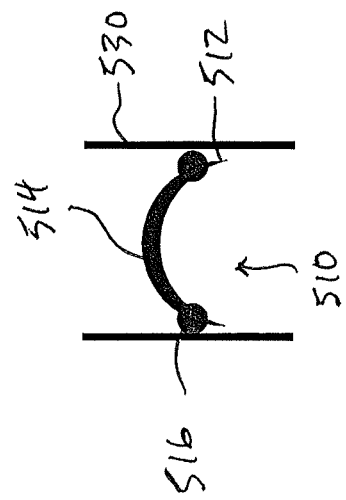
FIG. 8B depicts a cross sectional elevation view of the reactive stopper of FIG. 8A with the movable portion actuated.
Figure 8A:
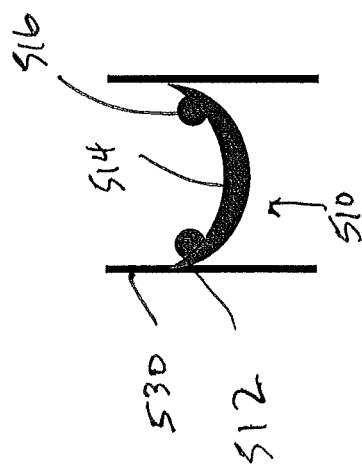
FIG. 8A depicts a cross sectional elevation view of yet another alternative exemplary version of a reactive stopper having a spherical cap shape with wall bumps.

FIGS. 8A-8B show yet another exemplary version of reactive stopper (510) having wall gripping features. Reactive stopper (510) has a generally spherical cap shape with a plurality of bumps (516) positioned on the concave portion of reactive stopper (510) shown in FIG. 5A. Reactive stopper (510) further comprises a contact portion (512) and a movable portion (514). A fluid seal is formed with cartridge body (530) when shown in the position demonstrated in FIG. 8A. Once sufficient pressure is applied to reactive stopper (510), movable portion (514) moves inverts as shown in FIG. 8B enabling fluid flow around reactive stopper (510). It will be appreciated that when movable portion (514) inverts, bumps (516) move outward to come into contact with cartridge body (530) as seen in FIG. 8B. Bumps (516) enable fluid flow around reactive stopper (510) while keeping reactive stopper (510) stable. It will be appreciated that other uses of reactive stopper (510) will be apparent to one of ordinary skill in the art in view of the teachings herein.

Figure 9B:
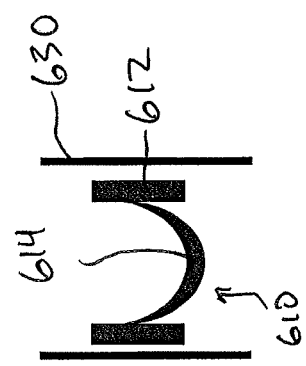
FIG. 9B depicts a cross sectional elevation view of the reactive stopper of FIG. 9A with the movable portion actuated.
Figure 9A:
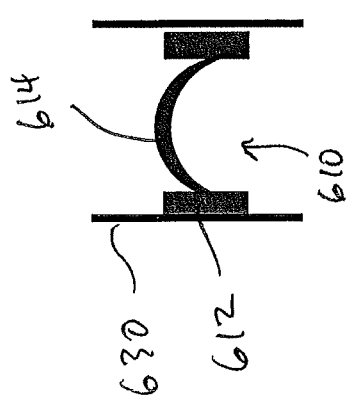
FIG. 9A depicts a cross sectional elevation view of yet another alternative exemplary version of a reactive stopper having a centered movable portion.

FIGS. 9A-9B show yet another exemplary version of reactive stopper (610) having a contact portion (612) and a movable portion (614) for use in cartridge body (630). In this exemplary version, movable portion (614) connects to contact portion (612) at approximately the longitudinal midpoint of contact portion (612). As a result, it will be appreciated that positioning the movable portion (614) at the longitudinal midpoint of contact portion (612) may be useful in terms of manufacturing, but other uses will be apparent to one of ordinary skill in the art in view of the teachings herein. It will further be appreciated that movable portion (614) may connect to contact portion (612) at any suitable position as would be apparent to one of ordinary skill in the art in view of the teachings herein.

Figure 10A:
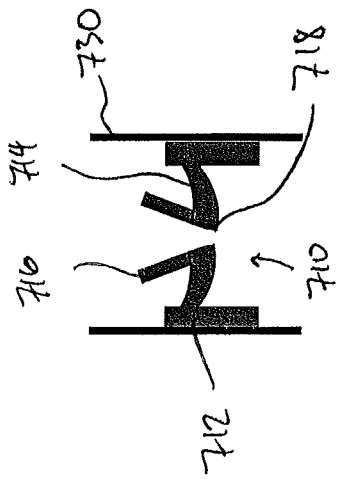
FIG. 10A depicts a cross sectional elevation view of yet another alternative exemplary version of a reactive stopper having a slit in the movable portion.
Figure 10B:
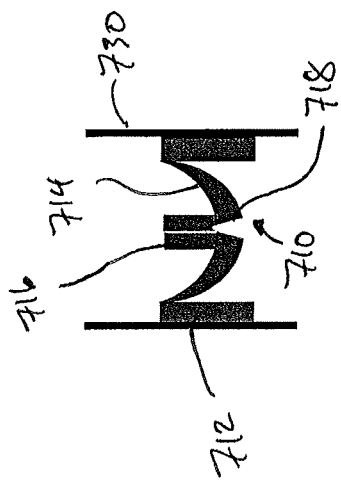
FIG. 10B depicts a cross sectional elevation view of the reactive stopper of FIG. 10A with the movable portion actuated.

FIGS. 10A-10B show yet another exemplary version of reactive stopper (710) comprising a contact portion (712), a movable portion (714), a sealed portion (716) and a slit (718). Slit (718) is shaped to be a cone-shaped slit, but it will be appreciated that any suitable shape for slit may be used as would be apparent to one of ordinary skill in the art in view of the teachings herein. Sealed portion (716) is sealed from fluid flow in FIG. 10A. As fluid pressure is applied to slit (718), slit (718) and sealed portion (716) open to allow fluid flow through reactive stopper (710). It will be appreciated that since movable portion (714) does not necessarily need to fully invert to allow fluid flow, less pressure may be required in order to enable fluid flow through reactive stopper (710). Sealed portion (716) in the exemplary version is depicted as a slightly elongate member operable to provide a fluid seal once pressed together. Sealed portion (716) may be sealed through a frictional grip or any other suitable method. Additionally, it will be appreciated that resilient pressure from the material itself may be applied to sealing portion (716) from contact portion (712) through movable portion (714). As seen in FIG. 10B, once sufficient pressure is applied, slit (718) opens and forces sealed portion (716) to open as well.

Figure 11A:
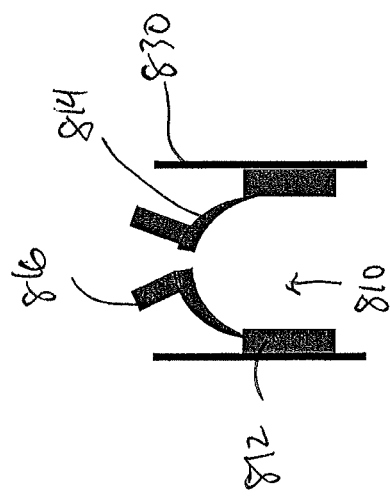
FIG. 11A depicts a cross sectional elevation view of yet another alternative exemplary version of a reactive stopper having a sealing member.
Figure 11B:
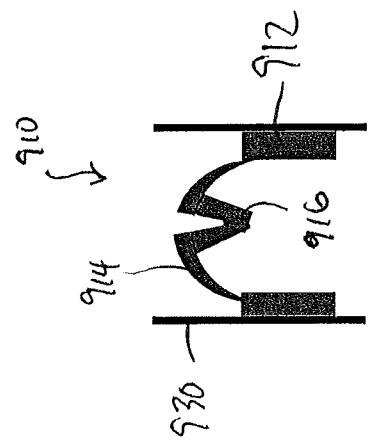
FIG. 11B depicts a cross sectional elevation view of the reactive stopper of FIG. 11A with the movable portion actuated.

FIGS. 11A-11B show another alternative exemplary version of reactive stopper (810) having a contact portion (812), a movable portion (814), a seal member (816), and connected portion (818). Reactive stopper (810) as seen in FIGS. 11A-11B may be positioned within a cartridge body (830). Connected portion (818) remains joined until reactive stopper (810) is to be actuated. FIG. 11A shows connected portion (818) sealed and as sufficient fluid pressure is applied to the convex surface of movable portion (814), connected portion (818) separates and causes movable portion to open as seen in FIG. 11B. As a result, fluid flow is allowed through reactive stopper (810).

Figure 12A:
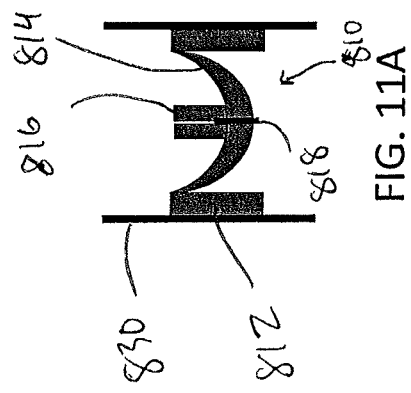
FIG. 12A depicts a cross sectional elevation view of yet another alternative exemplary version of a reactive stopper having engageable seal members.
Figure 12B:
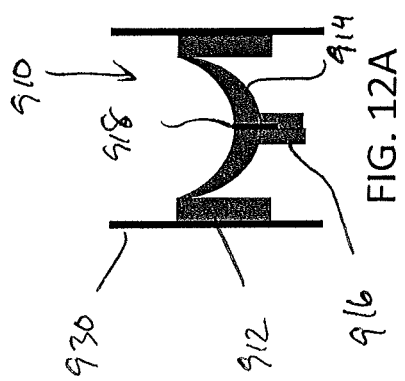
FIG. 12B depicts a cross sectional elevation view of the reactive stopper of FIG. 12A with the movable portion actuated and the seal members engaged.

FIGS. 12A-12B show yet another alternative exemplary version of reactive stopper (910) that comprises contact portion (912), a movable portion (914), a seal member (916), and a connected portion (918). Reactive stopper (910) may be positioned within a cartridge body (930). Unlike the version shown in FIGS. 11A-11B, seal member (916) extends downward from movable portion (914) as seen in FIG. 12A. As sufficient fluid pressure is applied to movable portion (914), movable portion (914) flips upward as shown in FIG. 12B, thereby allowing fluid flow through reactive stopper (910). Seal member (916) also engages as seen in FIG. 12B, which helps prevent parts of reactive stopper from flapping freely. As a result, fluid flow through reactive stopper (910) is allowed while maintaining connection at seal member (916), which may, for instance, provide added stability of reactive stopper (910).

Figure 13A:
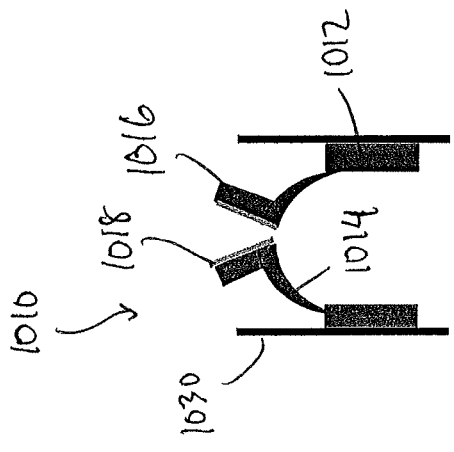
FIG. 13A depicts a cross sectional elevation view of yet another alternative exemplary version of a reactive stopper having a seal member and a seal region.
Figure 13B:
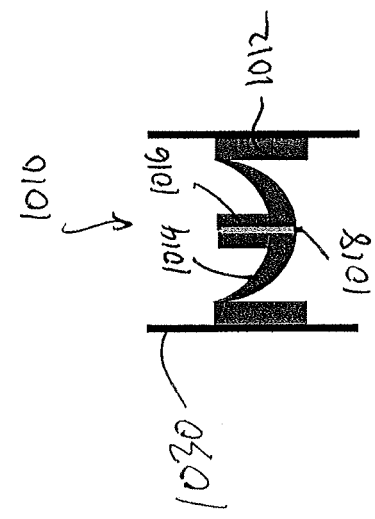
FIG. 13B depicts a cross sectional elevation view of the reactive stopper of FIG. 13A with the movable portion actuated.

FIGS. 13A-13B show yet another exemplary version of a reactive stopper (1010) having a contact portion (1012), a movable portion (1014), a seal member (1016), and a sealed region (1018). Reactive stopper (1010) is positioned within cartridge body (1030). Sealed region (1018) may be sealed using any suitable sealing method including heat sealing, chemical sealing, or any other suitable sealing means as would be apparent to one of ordinary skill in the art in view of the teachings herein. As fluid pressure is applied to movable portion (1014), sealed region (1018) disengages and movable portion (1014) flips upward as shown in FIG. 13B, thereby allowing fluid to flow through reactive stopper (1010).

Figure 14A:
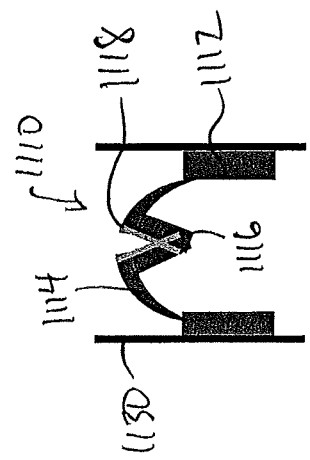
FIG. 14A depicts a cross sectional elevation view of yet another alternative exemplary version of a reactive stopper having an engageable seal member and a seal region.
Figure 14B:
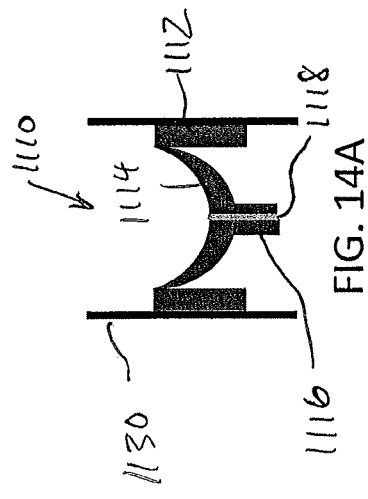
FIG. 14B depicts a cross sectional elevation view of the reactive stopper of FIG. 14A with the movable portion actuated and the seal members engaged.

FIGS. 14A-14B show a similar reactive stopper (1110) to that shown in FIGS. 13A-13B comprising a contact portion (1112), a movable portion (1114), a seal member (1116), and a sealed region (1118). Reactive stopper (1110) is positioned within cartridge body (1130). In contrast to the version shown in FIGS. 13A-13B, seal member (1116) extends downward from movable portion (1114). Once sufficient fluid pressure is applied to movable portion (1114) which breaks sealed region (1118), and movable portion (1114) inverts upwards, seal members (1116) link together as shown in FIG. 14B. As a result, fluid flow is permitted through reactive stopper (1110) yet movable portion (1114) is not permitted to loosely flap.

Figure 15A:
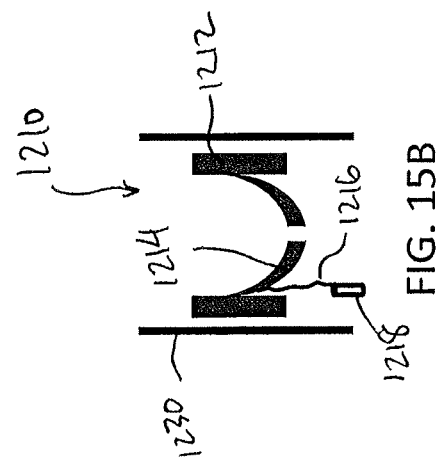
FIG. 15A depicts a cross sectional elevation view of yet another alternative exemplary version of a reactive stopper having a removable plug.
Figure 15B:
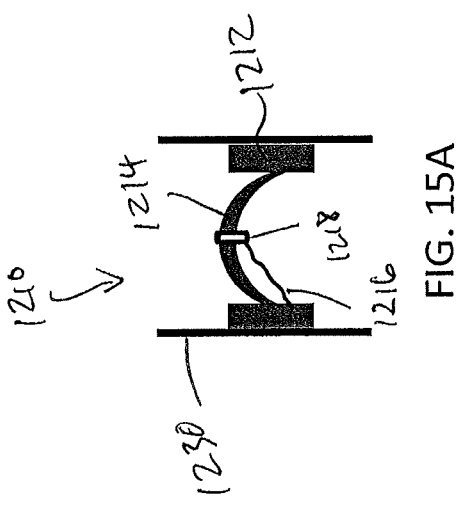
FIG. 15B depicts a cross sectional elevation view of the reactive stopper of FIG. 15A with the movable portion actuated and the plug removed.

FIGS. 15A-15B show yet another exemplary version of reactive stopper (1210) having a contact portion (1212), a movable portion (1214), a plug (1218), and a connecting device (1216). Reactive stopper (1210) is positioned within a cartridge body (1230). In the illustrated version, fluid pressure is applied to the concave version of movable portion (1214). Reactive stopper (1210) forms a fluid tight seal in FIG. 15A. When the user desires to reconstitute a substance by facilitating fluid flow through reactive portion (1210), plug (1218) is removed from movable portion (1214) by pulling connecting device (1216). In the exemplary version, plug (1218) is shaped to be a cylindrical plug, but any suitable shape for plug (1218) may be used as would be apparent to one of ordinary skill in the art in view of the teachings herein. Connecting device (1230) in the exemplary version comprises a tethering string, but any other suitable structure for connecting device (1230) may be used as would be apparent to one of ordinary skill in the art in view of the teachings herein. Once plug (1218) has been removed from movable portion (1214) as seen in FIG. 15B, fluid flows through reactive stopper (1210), and furthermore, the overall diameter of reactive stopper (1210) is decreased as contact portion (1212) no longer presses against cartridge walls (1230). As a result fluid is free to flow from one side of reactive stopper (1210) to the other.

Figure 16A:
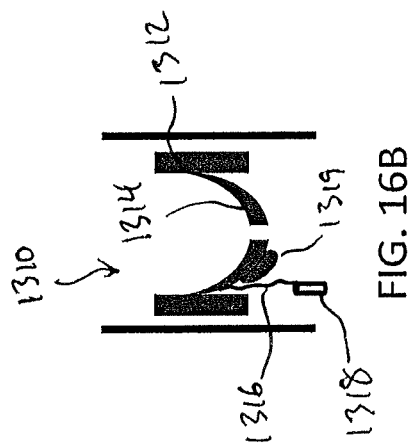
FIG. 16A depicts a cross sectional elevation view of yet another alternative exemplary version of a reactive stopper having a plug and a bump.
Figure 16B:
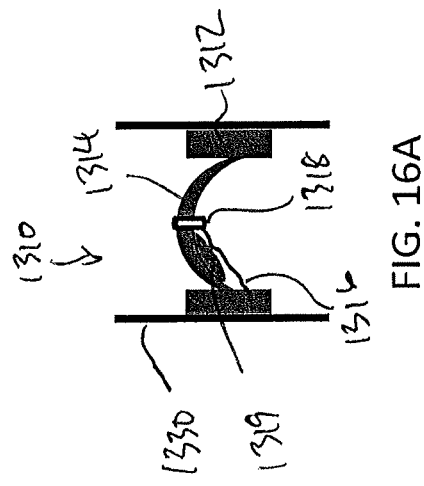
FIG. 16B depicts a cross sectional elevation view of the reactive stopper of FIG. 16A with the movable portion actuated and the plug removed.

FIGS. 16A-16B show yet another exemplary version of reactive stopper (1310) having a contact portion (1312), a movable portion (1314), a plug (1318), and a connecting device (1316). Reactive stopper (1310) is positioned within a cartridge body (1330). It will be appreciated that reactive stopper (1310) shown in FIGS. 16A-16B functions substantially similarly to reactive stopper (1210) shown in FIGS. 15A-15B. Furthermore, reactive stopper (1310) comprises a hump (1319) operable for use to serve to extend the distance connecting device (1316) must travel to be in connection with the plug (1318) when flipped. The hump (1319) or other geometries may serve as well to limit overfill by taking up void volume. These can be positioned to fill or open a void upon activation of reactive stopper (1310). The increased distance across the bottom surface of reactive stopper (1310) caused by the hump (1319) enables the opening of reactive stopper (1310) may be more easily facilitated because the distance connecting device (1316) travels will increase when hump (1319) is flipped.

Figure 17:
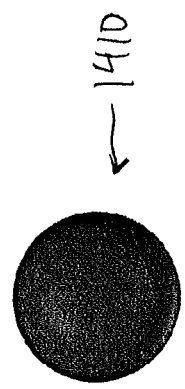
FIG. 17 depicts a top plan view of a merely exemplary alternative version of a reactive stopper having a circular shape.
Figure 18:
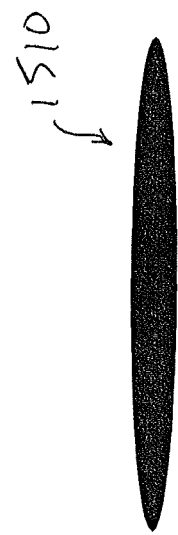
FIG. 18 depicts a side elevation view of a merely exemplary alternative version of a reactive stopper having an elliptical shape.
Figure 19:
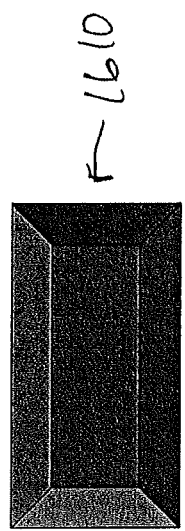
FIG. 19 depicts a side elevation view of a merely exemplary alternative version of a reactive stopper having a rectangular shape.
Figure 20:
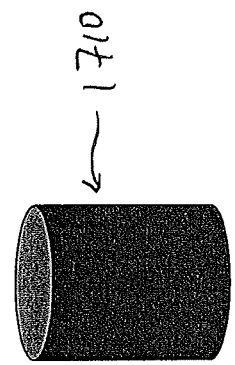
FIG. 20 depicts a side elevation view of a merely exemplary alternative version of a reactive stopper having a cylindrical shape.
Figure 21:
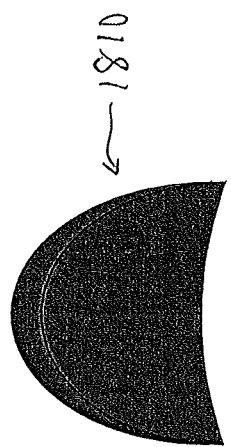
FIG. 21 depicts a side elevation view of a merely exemplary alternative version of a reactive stopper having a domed shape.

It will be appreciated that the overall reactive stopper as shown in any of FIGS. 1-16B as well as movable portions for use with the reactive stopper may have different suitable shapes. For instance, FIG. 17 depicts a circular and/or spherical shape (1410) for the reactive stopper and/or the movable portion. FIG. 18 depicts an elliptical shape (1510) for the reactive stopper and/or the movable portion. FIG. 19 shows a rectangular shape (1610) for the reactive stopper and/or the movable portion. FIG. 20 shows a cylindrical shape (1710) that may be used for the reactive stopper and/or movable portion. FIG. 21 depicts a domed shape (1810) that may be used for the reactive stopper and/or movable portion. While FIGS. 17-21 show some merely exemplary shapes that may be used with reactive stopper, it will be appreciated that any other suitable shapes may be used as would be apparent to one of ordinary skill in the art in view of the teachings herein.

FIG. 22A depicts an exemplary stopper or plunger (2100) that can be shaped to achieve the desired changes in dimensions when forcing it to change from its "natural" or "resting" or "unlocked" state. Stopper or plunger (2100) is operable generally to fit in a container or syringe. Stopper or plunger (2100) is further configured to glide or travel from one point within the container or syringe such that stopper or plunger (2100) is able to urge a material within container or syringe. FIG. 22A is an exemplary stopper or plunger (2100) in its unlocked, natural, or resting state. Its diameter is determined generally by the required diameter to maintain contact with the walls of a container to expel the contents as it moves forward, though it will be understood that other suitable diameters may be used as would be apparent to one of ordinary skill in the art in view of the teachings herein.

FIG. 22B depicts the same plunger (2100) in FIG. 22A but in the "locked" position. FIG. 22B shows plunger (2100) flipped in on itself such that center portion (2102) inverts. The result is that the diameter (2103) of plunger (2100) is larger in FIG. 22B than in FIG. 22A. When pressure is applied to center portion (2102) in FIG. 22B, the diameter (2103) attempts to expand by urging sides (2101) against an exterior container wall such as the walls of a syringe thereby increasing the friction. Pressure can be applied to center portion (2102) in the form of a push rod, pressure from a liquid, such as in a dual chamber cartridge system or any other form of applying force. Once enough pressure is applied to center portion (2102), plunger or stopper (2100) will "flip" back to its unlocked (FIG. 22A) state and surface (2104) will now maintain the seal against the container wall such that the glide force is optimized for smooth ejection of the contents in the container. In other words, surface (2104) applies a pressure against the container that facilitates stopper or plunger (2100) gliding through the container. In some versions, the pressure may include less pressure overall while still allowing stopper or plunger (2100) to advance.

It will be understood that in some versions, a lubricant may be used with stopper or plunger (2100). For instance, parts of stopper or plunger (2100) may be coated or covered in a lubricant such that friction between stopper or plunger (2100) and the container holding stopper or plunger (2100) is reduced. Furthermore, in some versions, particular portions of stopper or plunger (2100) may be covered with a lubricant. For instance, referring to FIGS. 22A-22B, lubricant may be applied only to surface (2104) such that when in the state of FIG. 22B, the lubricated portion of stopper or plunger (2100) does not touch the walls of the container holding stopper (2100). However, once stopper or plunger (2100) actuates to assume the position in FIG. 22A, the lubricated surface (2104) comes in contact with the walls of the container, thereby further lowering the friction between surface (2104) and the side walls than would be the case if lubricant were not applied.

FIG. 23A shows another version of a stopper or plunger (2110) where the locking component (2112) is separate from another sealing component (2114) which is operable to maintain a seal after activation. For instance, the sealing component (2114) is shown in a locked state in FIG. 23B which urges sealing component (2114) outward. An intermediate member (2116) is positioned between locking component (2112) and sealing component (2114). It will be appreciated that intermediate member (2116) may be operable to flip sealing component (2114) at a lesser force than the version shown in FIGS. 22A and 22B. It will be appreciated that stopper (2110) may be used in a dual chambered system facilitating reconstitution as stopper (2110) moves through a bypass region, or alternatively that stopper (2110) may be used to urge material to advance within a single chamber device.

Figure 24D:
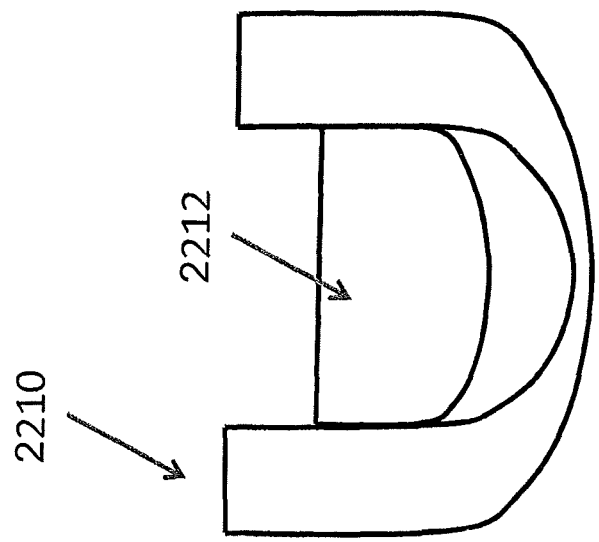
FIG. 24D depicts a side, cross sectional view of the stopper of FIG. 24C with the actuating component advanced with the stopper in an unlocked state.

FIGS. 24A-24D depicts another stopper or plunger (2200) that can achieve similar results as described for instance in reference to FIG. 22A. FIG. 24A depicts an "unlocked" shape, which could represent stopper (2200) being removed from a mold and biased to assume the shape shown in FIG. 24A. Again, the diameter marked (2201a) is set to be the appropriate diameter for the appropriate glide force required after the plunger/stopper (2200) has been unlocked. It will be understood that a wall (2203) may include or be lined with ribs or rings to promote proper pressure being exerted by stopper (2200) against the walls of a syringe or container.

FIG. 24B shows the "locked" position of stopper (2200) of FIG. 24A. Plunger or stopper (2200) has been folded in on itself which results in diameter (2201b), which is greater than (2201a) which increases the friction against the container walls, thus locking it into place. When pressure is applied to point (2202), the plunger (2200) unfolds itself and unlocks to the position shown in FIG. 24A such that plunger (2200) is able to glide with less force required through a syringe or other suitable container.

Figure 24C:
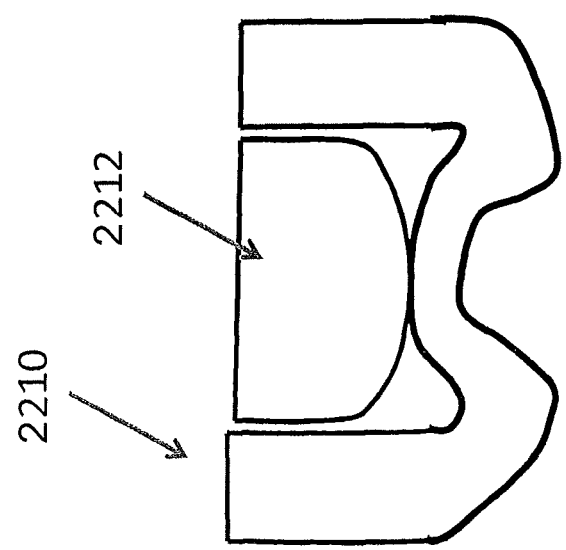
FIG. 24C depicts a side, cross sectional view of the stopper of FIG. 24A with an actuating component with the stopper in a locked state.

FIG. 24C shows a similar version of a stopper or plunger (2210) to the stopper (2200) of FIGS. 24A and 24B in which an assembly with an actuating component (2212) is used to activate the unlocking mechanism. In particular, in FIG. 24C, actuating component (2212) is seated within stopper (2210) with stopper (2210) in a locked state. In FIG. 24D, actuating component (2212) has pressed against stopper (2210), thereby actuating stopper (2210) to the position shown in FIG. 24D. Furthermore, it will be understood that stopper (2210) in FIG. 24C has a generally wider radius that stopper (2210) in FIG. 24D. As a result, stopper (2210) in 2C is operable to apply outward pressure against walls of a container or syringe.

FIGS. 25A-25B depict another embodiment of a rubber plunger or stopper (2300) achieving a similar locking and unlocking action. FIG. 25A show the unlocked position of the plunger (2300) as it is at rest. FIG. 25B shows the plunger (2300) in the locked position with flanges (2301) flipped back into the locked position, which could, for instance, be held in place by the walls of the container in which plunger (2300) is contained within. The diameter (2302a) in the unlocked position grows to a larger diameter (2302b) which applies more force and friction against the container walls. When force is applied to side (2303), the flanges (2301b) are forced against the wall of the container until a threshold force flips the flanges (2301b) back to their original (2301a) form. Once the plunger (2300) is unlocked, it is able to move along the container at the desired glide force.

Figures 26A, 26B:
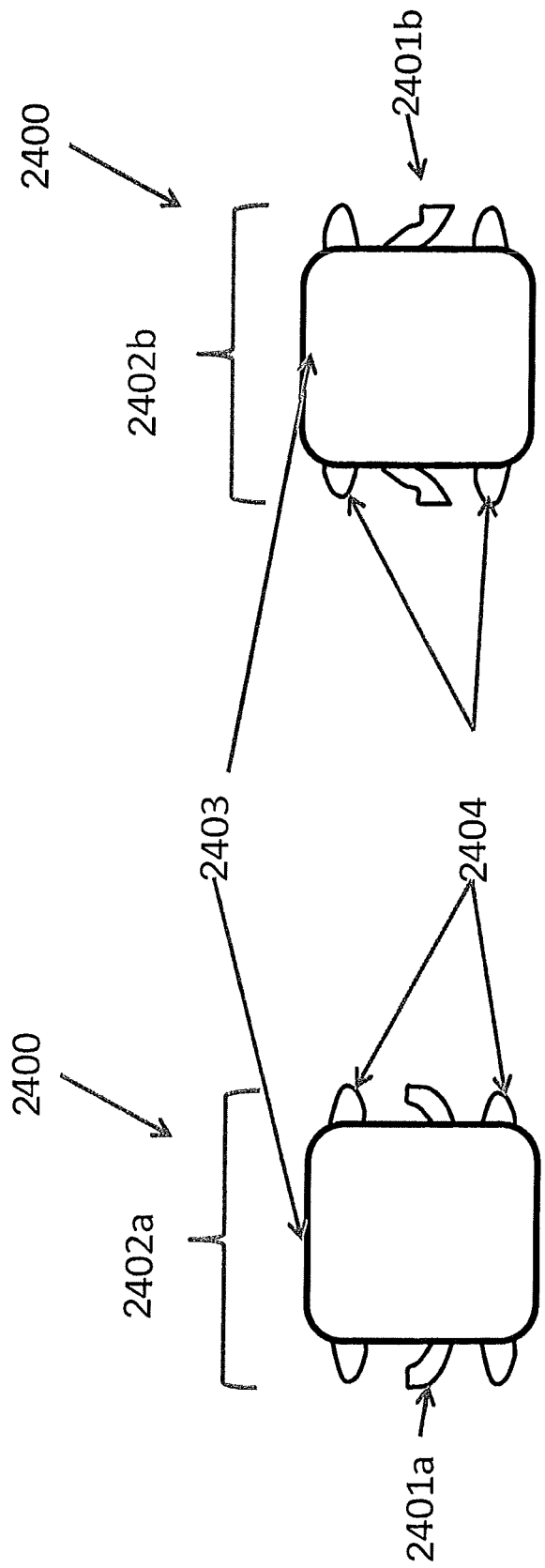
FIG. 26A depicts a side, elevation view of an exemplary alternative version of a stopper in an unlocked position with side flanges.
FIG. 26B depicts a side, elevation view of the stopper of FIG. 26A in a locked position.

FIGS. 26A-26B depict another rendition of a rubber plunger or stopper (2400) achieving a similar locking action as the above described versions. FIG. 26A shows the unlocked position of the plunger (2400) as it is at rest. FIG. 26B shows the plunger (2400) in the locked position with flanges (2401) flipped back into the locked position (2401b) and held in place by the walls of the container. The diameter (2402a) in the unlocked position grows to a larger diameter (2402b) which applies more force and friction against the container walls. When force is applied to side (2403), the flanges (2401b) are forced against the wall of the container until a threshold force flips the flanges back to their original (2401a) form. Once the plunger is unlocked, it is able to move along the container at the desired glide force. FIG. 26A differs from FIG. 25A in one aspect in that the locking flanges (2401a) and (2401b) are isolated between seals (2404) which may promote better sealing and gliding of the plunger (2400).

Figures 27A, 27B, 27C:
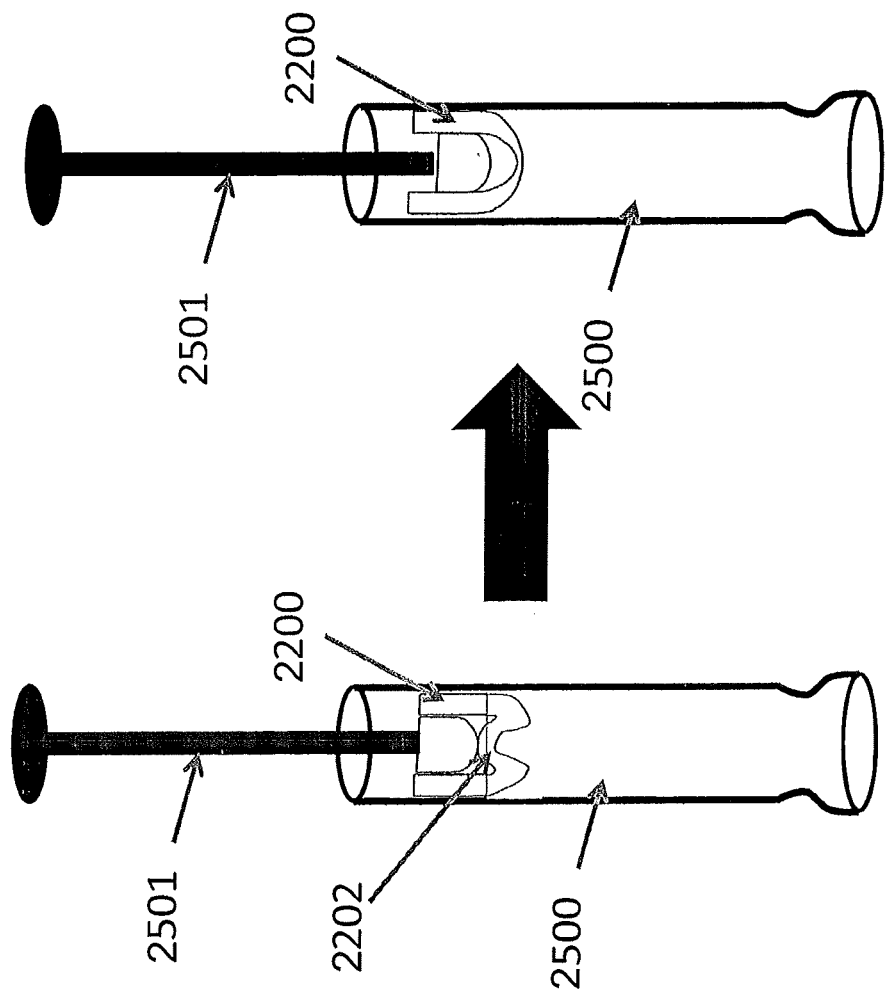
FIG. 27A depicts a side, cross sectional view of the stopper of FIG. 24A inserted into a syringe.
FIG. 27B depicts a side, cross sectional view of the stopper and syringe of FIG. 27A with the stopper unlocked.
FIG. 27C depicts a side, cross sectional view of the stopper and syringe of FIG. 27A with the stopper advanced.

FIGS. 27A-27C depict one exemplary sequence of events that may take place using the design of plunger (2200) depicted in FIG. 24A when placed in a syringe (2500). Push rod (2501) applies the force mentioned above on point (2202). The user may apply force distally along push rod (2501) such that plunger (2200) flips to the position shown in FIG. 27B. It will be understood that in changing from the position shown in FIG. 27A to FIG. 27B, plunger (2200) reduces the amount or outward pressure applied to walls of syringe (2500). As a result, the reduced force against the walls of syringe (2500) is operable to promote gliding of plunger (2200) through syringe (2500) as seen in FIG. 27C. It will be appreciated that the same push rod (2501) and syringe (2500) may be used with any versions depicted in FIGS. 22A-26B. It should be noted that other types of actuation mechanisms including springs, battery expansions, pressurized cylinders, gravitational or centripetal force, or any other suitable actuation mechanism could be used as would be apparent to one of ordinary skill in the art in view of the teachings herein.

FIGS. 28A-28D depict an exemplary sequence of events that may take place using the locking stopper (2602), which is substantially similar to plunger (2200) of FIG. 24A, in a dual chamber cartridge (2600). It will be appreciated that in cartridge (2600), the lower portion of cartridge (2600) may be in a vacuum state. Due to assistance from the vacuum in the lower portion of cartridge (2600), it will be understood that a relatively smaller force (e.g., "least force") is required to advance stopper (2600) to bypass region (2603). Furthermore, greater force (e.g., "intermediate force") may be required to advance stopper (2600) past bypass region (2603), yet that force may still be less than required to switch stopper (2600) from a locked to an unlocked state, which at least in some instances, requires relatively the most force to apply (e.g., "max force"). Instead of the push rod (2604) directly contacting the locking stopper (2602), pressure is transferred from the push rod (2604) to the locking stopper (2602) via liquid in chamber (2601). Once the locking stopper (2602) unlocks with application of a force as seen in FIG. 28B, then the wall friction and force required to advance stopper (2602) will be reduced. This will allow for easier pushing into the bypass region (2603). In the case where one chamber is under higher pressure than the other or one chamber is partially in vacuum (for instance the lower chamber may be in vacuum), the unlocking of stopper (2602) is sufficient to cause the vacuum or pressure differential to pull and or push this unlocked form of the locking stopper (2602) into the bypass region by the suction force of the vacuum or pressure of the high pressure without additional actuation as seen in FIG. 28C. Once stopper (2602) traverses the bypass region (2603) the materials in the two chambers will mix and the pressures will equalize. Then the stopper (2602) will require additional force as described above to push stopper (2602) forward since there is no longer a pressure differential creating a vacuum or pushing stopper (2602) forward. In many scenarios, especially cartridges vials or syringes with large cross sectional areas, the force required to unlock and the force required to advance the unlocked plunger (2602) after the pressures in the chambers equalize, could both be engineered to be a suitable nominal force to enable an administration of components at a force after reconstitution that is in the range of ¼ lb to 10 lbs. In some scenarios, the locking and advancing after pressure equalization in this scenario could work between 1-3 lbs such that a user could do both steps by hand.

FIGS. 29A-29B depict another exemplary version of a locking stopper or plunger (2700). In this version a closed cell sponge like feature enables at least a part of the stopper (2700) to expand in the presence of a pressure differential. These expanded cells (2701) could expand as seen in FIG. 29A because they may be placed in a bypass syringe with a lyophilized component chamber, which may be at a partial vacuum. Additionally, one chamber could be at a normal pressure and the other chamber could be at a higher pressure. Once the force is applied such that the foam or sponge like stopper (2700) moves to a position within the chamber where the pressures in the chambers can equalize then the cells (2701) acted upon by the higher net pressure in that region will collapse as seen in FIG. 29B to shrink the stopper (2700) diameter and thus reduce the friction force against the walls of the drug container.

FIGS. 30A-30B depict another exemplary version of a locking stopper with a flexible walled drug delivery housing (2803) that has the ability to unlock an at least partially flexible stopper (2801), which maintains a seal against the wall when unlocked even though the force to move stopper (2801) relative to housing (2803) is reduced. An unlocking outer sleeve component (2802) is moved to release the additional compression force on the stopper (2801) by compression of the delivery housing (2803). FIG. 30A depicts a locked state, and FIG. 30B depicts an unlocked state.

FIGS. 30C and 30D depict an outer unlocking locking stopper (2804) that is comprised of at least a partially ridged portion that does not seal against the housing (2803) after the compressive force is released. This could enable flow around the stopper (2804) to mix multiple components. FIG. 30C shows outer sleeve component (2802) around stopper (2804) and compressing housing (2803). In FIG. 30D, outer sleeve component (2802) is removed such that housing (2803) expands slightly and stopper (2804) is no longer sealed against the walls of housing (2803).

Figure 31:
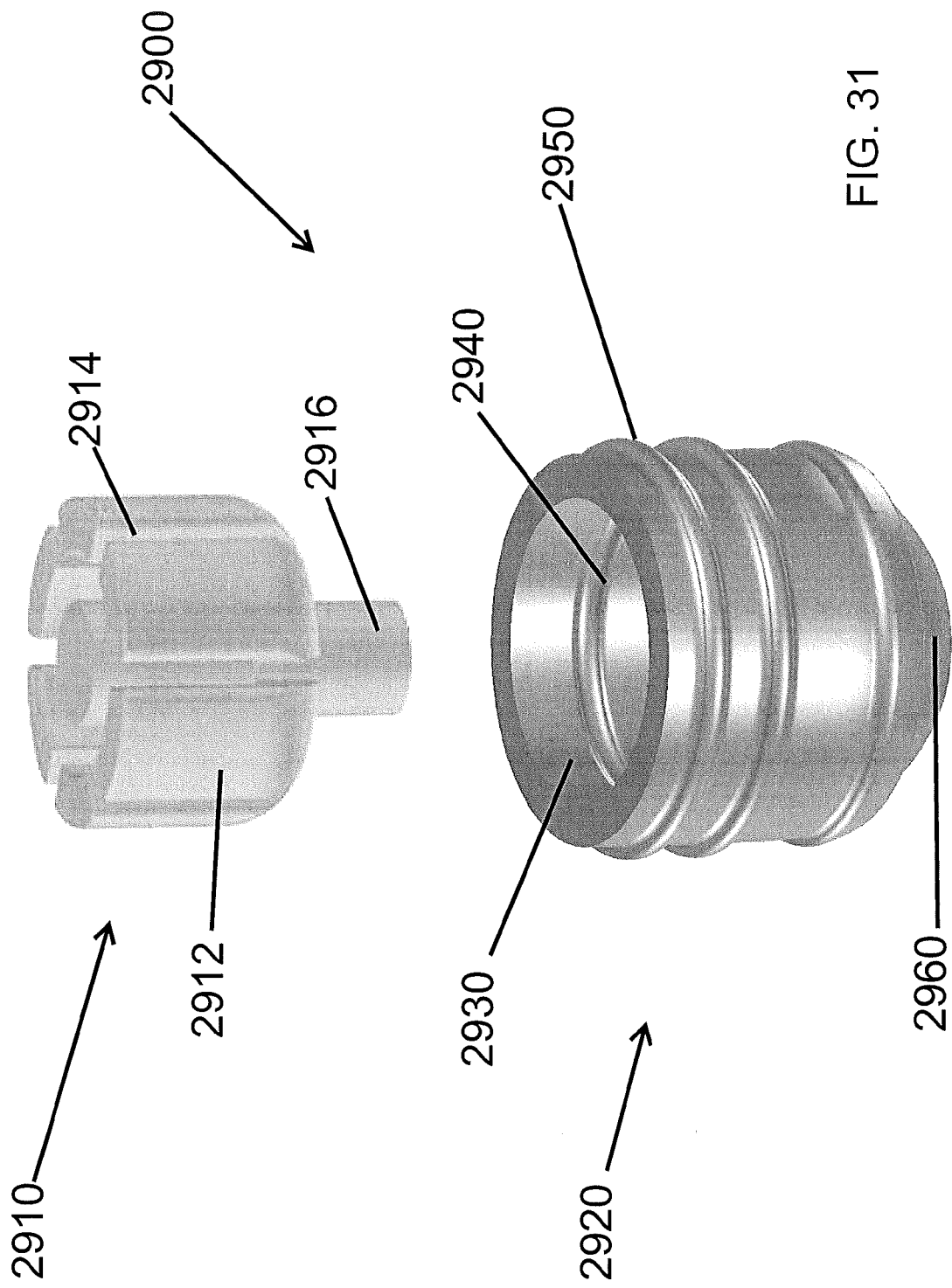
FIG. 31 depicts a side, perspective view of yet another exemplary alternative plunger.

FIG. 31 shows an exemplary alternative plunger (2900) operable to selectively activate to provide fluid communication within a syringe or cartridge. Plunger (2900) comprises a first plunger portion (2920) and a second plunger portion (2910). First plunger portion (2920) has a cup-like shape as seen in the cross sectional view shown in FIG. 32. First plunger portion (2920) comprises a domed tip (2960), one or more ribs (2950), one or more interior grooves (2940), defines an opening (2930), and further defines a tip opening (2970). Second plunger portion (2910) comprises outer walls (2912), one or more bypasses (2914), and a plug (2916).

One or more ribs (2950) are operable to grip the sides of a syringe or cartridge. It will be understood that one or more ribs (2950) may be operable to provide an outward force on a syringe or cartridge operable to maintain the longitudinal position of plunger (2900) within a syringe or cartridge. That force may be overcome by providing sufficient force using plunger driver or push rod, which provides force longitudinally along the syringe or cartridge as will be shown below. In the exemplary version, three ribs (2950) are shown, but it will be appreciated that any suitable number of ribs (2950) may be used as would be apparent to one of ordinary skill in the art in view of the teachings herein. One or more interior grooves (2940) are operable to receive second plunger portion (2910). Domed tip (2960) includes a flexible material operable to retract into opening (2940) of first plunger portion (2920).

Second plunger portion (2910) is operable to fit inside opening (2940) of first plunger portion (2920). Plug (2916) is operable to fit within and block tip opening (2970). Outer walls (2912) may have a profile that complements one or more interior grooves (2940) and/or the interior of first plunger portion (2920). One or more bypasses (2914) are operable to allow fluid flow through second plunger portion (2910). Once second plunger portion (2910) is placed within first plunger portion (2920), plug (2916) stops fluid flow through domed tip (2960). Fluid pressure may be urged through one or more bypasses (2914) which may provide sufficient pressure to allow domed tip (2960) to distally flex outward and separate from plug (2916). Thereafter, fluid is able to flow through tip opening (2970). It will be appreciated that such an opening (2970) may be formed in any suitable location on first plunger portion (2920).

Figure 33A:
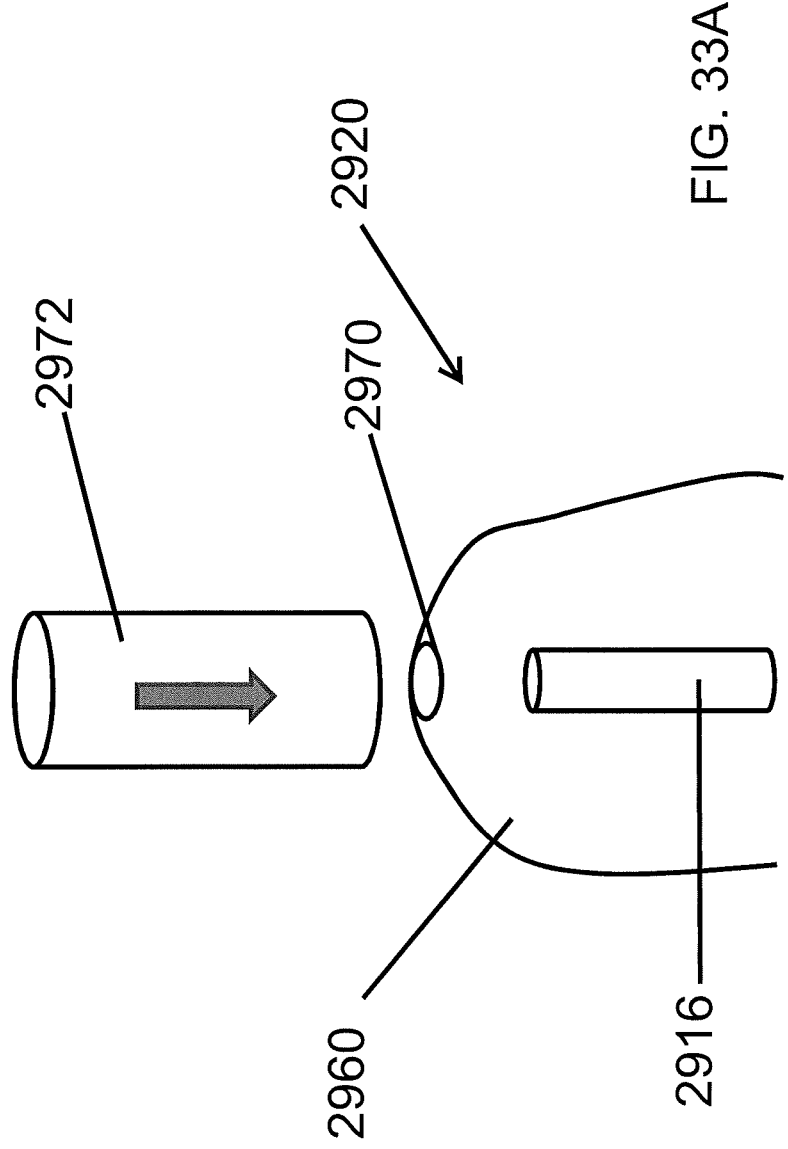
FIG. 33A depicts a side, perspective view of the plunger of FIG. 31 with a loading tool.
Figure 33B:
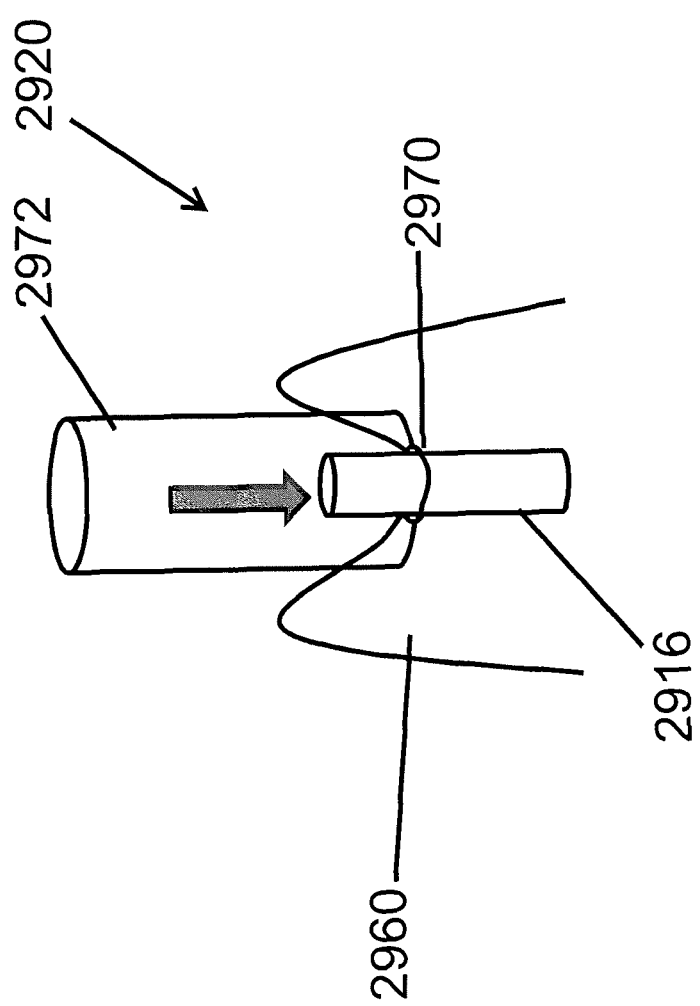
FIG. 33B depicts a side, perspective view of the plunger of FIG. 31 with the loading tool deforming the first plunger portion.
Figure 33C:
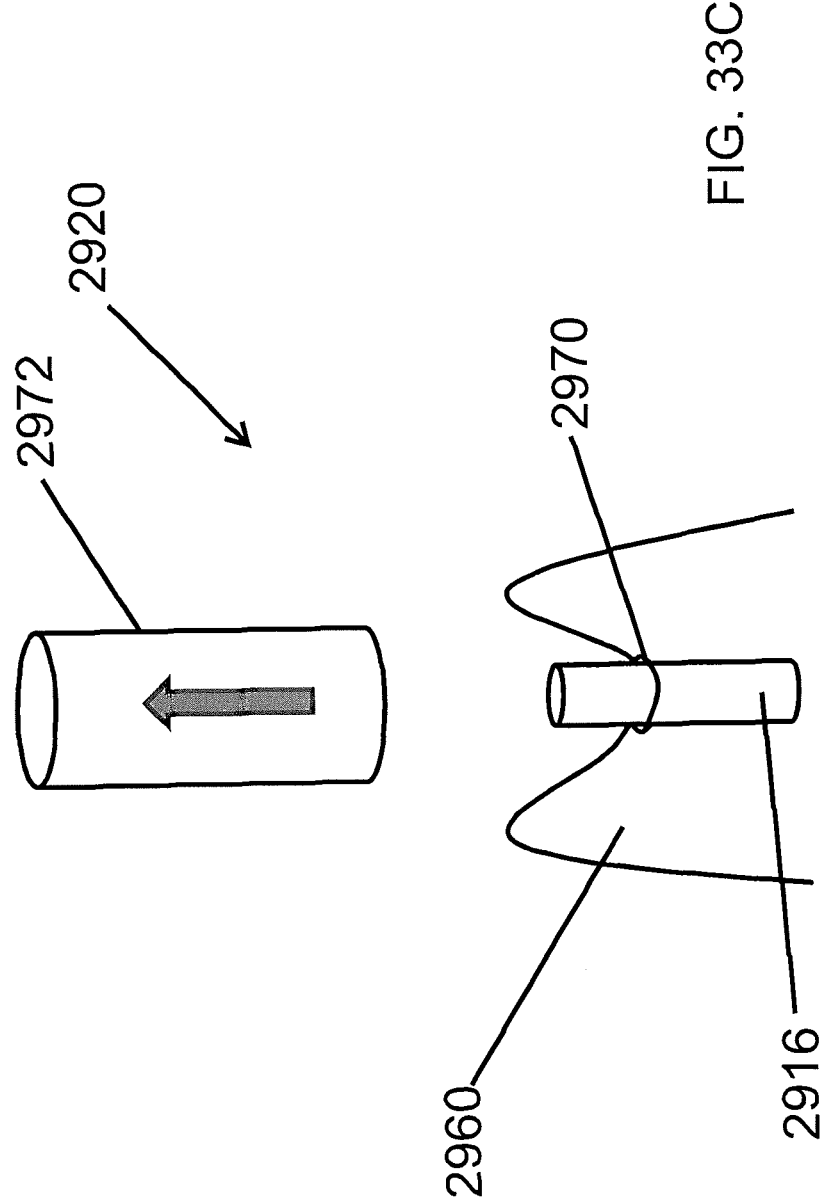
FIG. 33C depicts a side, perspective view of the plunger of FIG. 31 with the loading tool removed from the first plunger portion.

It will be understood that plunger (2900) may be prepared for use in a variety of ways. For instance FIGS. 33A-33C show first plunger portion (2920) in a flipped over orientation and showing only plug (2916) of second plunger portion (2910). A loading tool (2972) is operable to couple tip opening (2720) with plug (2916) by deforming domed tip (2960) in the direction of plug (2916). FIG. 33A shows loading tool (2972) ready to apply the force to domed tip (2960). FIG. 33B shows loading tool (2972) pressed against domed tip (2960) and causing domed tip (2960) to deform toward plug (2916). Plug (2916) plugs tip opening (2970). Thereafter, as seen in FIG. 33C, loading tool (2972) is removed, leaving tip opening (2970) plugged by plug (2916). Plunger (2900) may then be loaded into a syringe or cartridge.

Figure 34A:
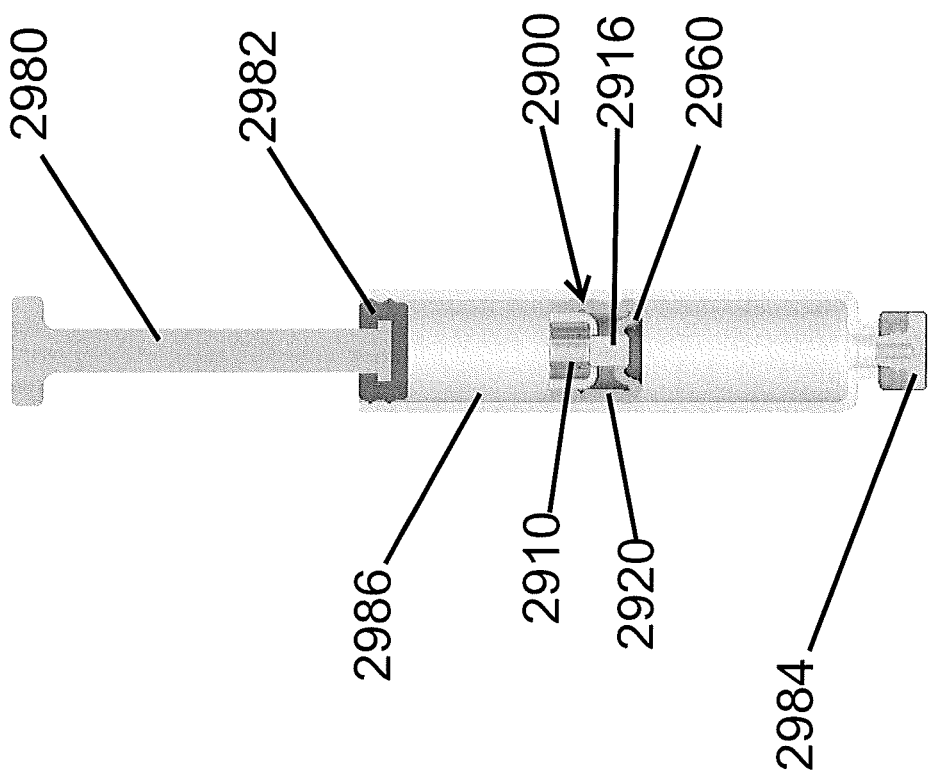
FIG. 34A depicts a side, cross sectional view of the plunger of FIG. 31 within a cartridge and in the locked position.
Figure 34B:
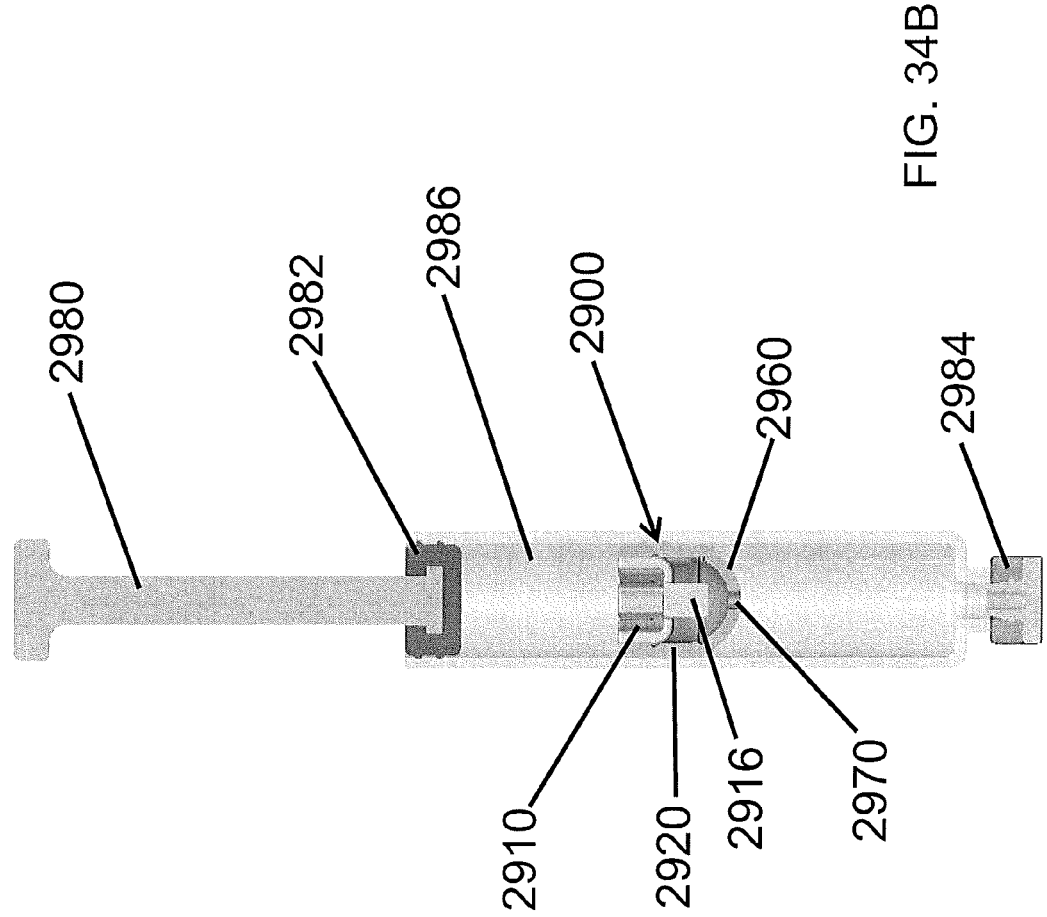
FIG. 34B depicts a side, cross sectional view of the plunger of FIG. 31 within a cartridge and in the unlocked position.

FIGS. 34A-34B show plunger (2900) placed in an exemplary cartridge (2986). Cartridge (2986) includes a plunger driver (2980) with a distal end (2982) where plunger driver (2980) is operable to distally advance through cartridge (2986). A distal plug (2984) caps cartridge (2986) until cartridge (2986) is ready for use. FIG. 34A shows plunger (2900) in a locked state where fluid flow does not occur through plunger (2900). When the user wishes to activate plunger (2900), distal force is applied to plunger driver (2980), which causes distal end (2982) to advance and urge fluid through second plunger portion (2910). As seen in FIG. 34B where plunger (2900) is in an unlocked state, domed tip (2960) separates from plug (2916) allowing fluid to flow through plunger (2900). Thereafter, the user may further advance plunger driver (2980) distally through cartridge (2986), which may cause distal end (2982) to contact and advance the opened or unlocked stopper (2900) distally which helps to urge fluid from cartridge (2986).

Figure 35A:
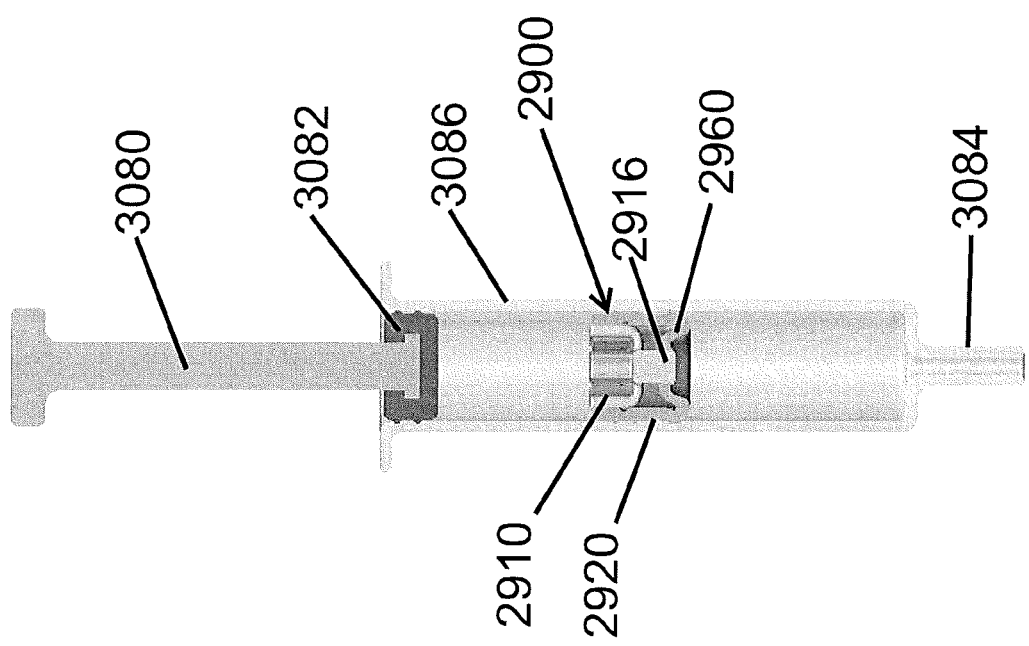
FIG. 35A depicts a side, cross sectional view of the plunger of FIG. 31 within a syringe and in the locked position.
Figure 35B:
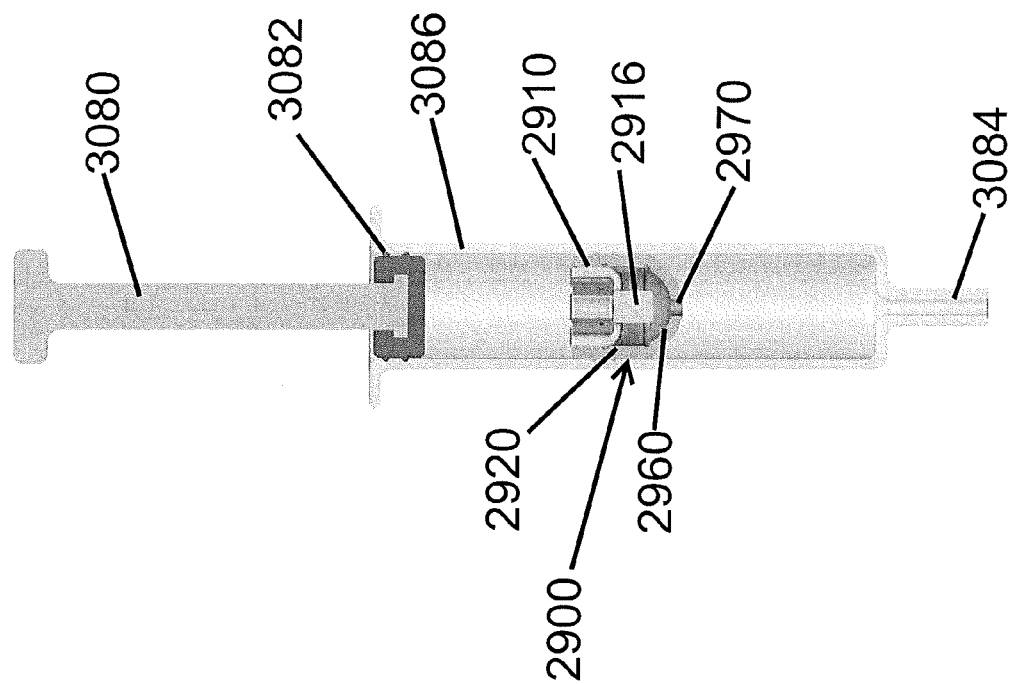
FIG. 35B depicts a side, cross sectional view of the plunger of FIG. 31 within a syringe and in the unlocked position.

FIGS. 35A-35B show plunger (2900) placed in an exemplary syringe (3086). Syringe (3086) includes a plunger driver (3080) with a distal end (3082) where plunger driver (3080) is operable to be distally advanced through syringe (3086). A distal coupling (3084) is operable to engage a needle or tube or any other suitable structure that the user may wish to use with syringe (3086). FIG. 35A shows plunger (2900) in a locked state where fluid flow does not occur through plunger (2900). When the user wishes to activate plunger (2900), distal force is applied to plunger driver (3080), which causes distal end (3082) to advance and urge fluid through second plunger portion (2910). As seen in FIG. 35B where plunger (2900) is in an unlocked state, domed tip (2960) separates from plug (2916) allowing fluid to flow through plunger (2900). Thereafter, the user may further advance plunger driver (3080) distally through syringe (3086), which may cause distal end (3082) to contact and advance the opened or unlocked stopper (2900) distally which helps to urge fluid from syringe (3086).

It will be appreciated that plunger (2900) may include a variety of shapes and configurations as would be apparent to one of ordinary skill in the art in view of the teachings herein. For instance, FIG. 36 shows an exemplary alternative version of a plunger (3100) having a first plunger portion (3120) and a second plunger portion (3110). Second plunger portion (3110) includes internal bypasses (3114) that function in a similar way to one or more bypasses (2914) shown in FIG. 31. Second plunger portion (3110) includes a plug (3116) having a ribbed profile operable to seal plug (3116) within tip opening (3170) of domed tip (3160). As also seen in the exemplary version, second plunger portion (3110) is operable to engage first plunger portion (3120) through a plurality of internal ribs (3140).

FIG. 37 shows an exemplary alternative version of a plunger (3200) having a first plunger portion (3220) and a second plunger portion (3210). Second plunger portion (3210) includes a shallower shaped internal bypass (3214)

than internal bypass (3114) of FIG. 36. Second plunger portion (3210) also includes a plug (3216) having a generally flat or straight profile. Second plunger portion (3210) in the illustrated version has a single ribbing (3240) operable to engage the interior of first plunger portion (3420). Tip opening (3270) of domed tip (3260) is operable to selectively engage plug (3216).

Figure 38:
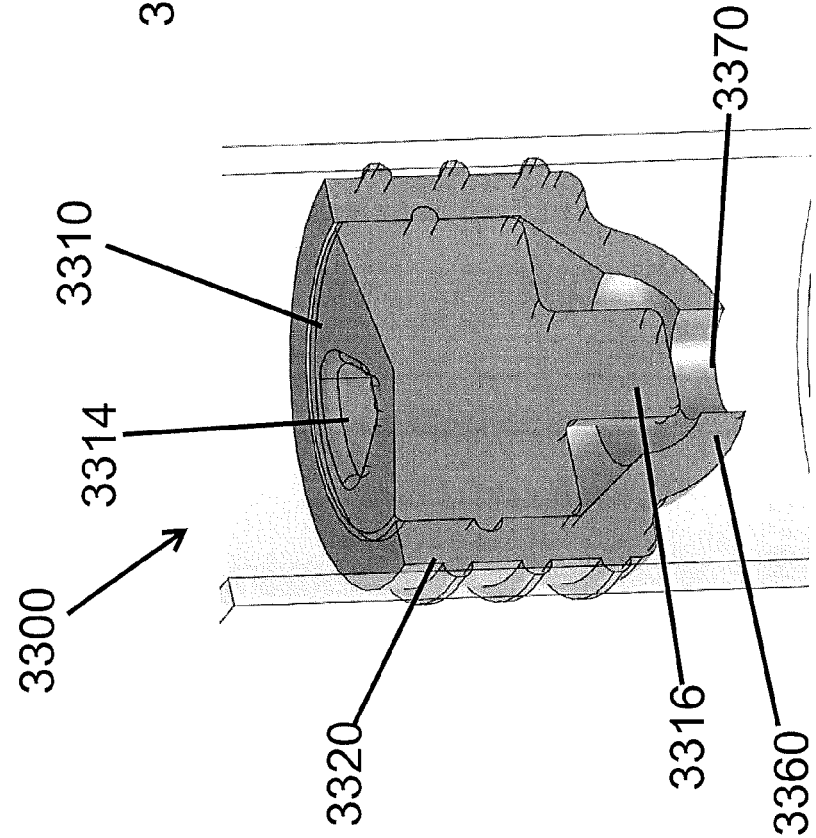
FIG. 38 depicts a side, cross sectional, perspective view of an exemplary alternative plunger with a narrower fluid bypass.

FIG. 38 shows an exemplary alternative version of a plunger (3300) having a first plunger portion (3320) and a second plunger portion (3310). Second plunger portion (3310) includes a smaller bypass region (3314) than internal bypass (3114) of FIG. 36. Second plunger portion (3310) also includes a plug (3316) having a generally flat or straight profile. Second plunger portion (3310) in the illustrated version has a single ribbing (3340) operable to engage the interior of first plunger portion (3420). Tip opening (3370) of domed tip (3360) is operable to selectively engage plug (3316).

Figure 39:
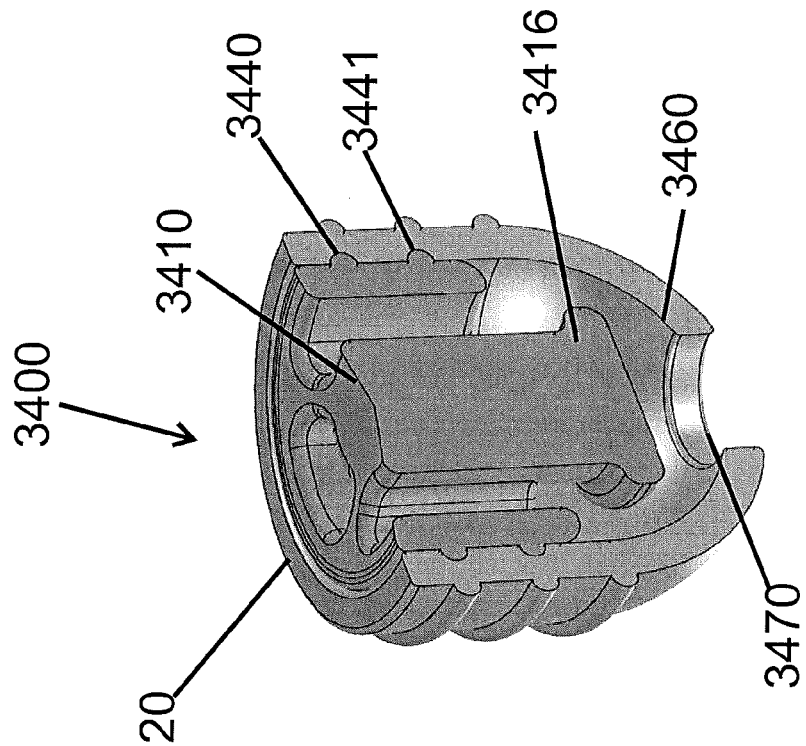
FIG. 39 depicts a side, cross sectional, perspective view of an exemplary alternative plunger with a thick plug.

FIG. 39 shows an exemplary alternative version of a plunger (3400) having a first plunger portion (3420) and a second plunger portion (3410). Second plunger portion (3410) includes a bypass region (3414). Second plunger portion (3410) also includes a plug (3416) having a thicker diameter than plug (3116) shown in FIG. 36. Second plunger portion (3410) in the illustrated version has a plurality of ribs (3440) operable to engage grooves (3441) of first plunger portion (3420). Tip opening (3470) of domed tip (3460) is operable to selectively engage plug (3416).

Figure 40:
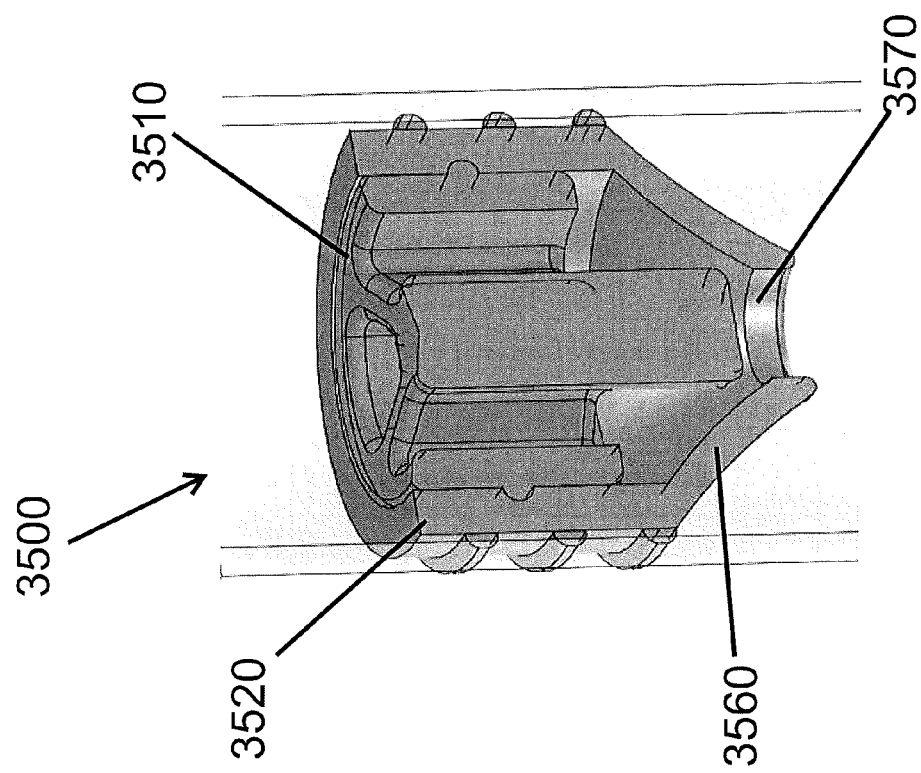
FIG. 40 depicts a side, cross sectional, perspective view of an exemplary alternative plunger with a frustoconical tip.

FIG. 40 shows an exemplary alternative version of a plunger (3500) having a first plunger portion (3520) and a second plunger portion (3510). Second plunger portion (3510) includes a bypass region (3514). Second plunger portion (3510) also includes a plug (3516). Tip opening (3570) of domed tip (3560) is operable to selectively engage plug (3516). Domed tip (3560) of the illustrated version has a frustoconical shape rather than the curved profile of domed tip (3160) of FIG. 36.

Figure 41:
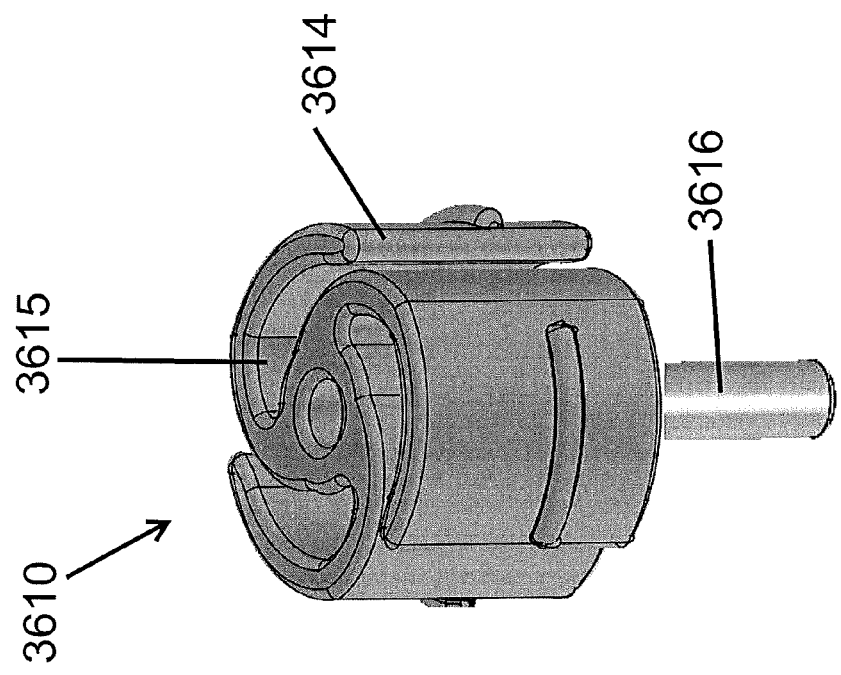
FIG. 41 depicts a side, cross sectional, perspective view of an exemplary alternative plunger with curved bypass fins.

FIG. 41 shows an exemplary alternative version of a second plunger portion (3610). Second plunger portion (3610) includes a plurality of curved bypass fins (3614) which define bypass regions (3615) within second plunger portion (3610). Second plunger portion (3610) also includes a plug (3616) selectively removable from second plunger portion (3610). It will be appreciated that second plunger portion (3610) may be used with any of the first plunger portions (3520, 3420, 3320, 3220, 3120, 2920) shown above in FIGS. 31-40.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings

What is claimed is:

1. An apparatus comprising a plunger configured to fit in a cartridge or syringe, the plunger apparatus comprising:
    a first plunger portion comprising:
    an open end;
    a deflection portion opposite the open end and including an opening; and
    an outer, circumferential, contact portion configured to contact an inner surface of the cartridge or syringe; and
    a second plunger portion configured for receipt within the first plunger portion and comprising:
    a central plug;
    at least one outer wall of the second plunger portion configured to contact an inner surface of the first plunger portion; and
    at least one channel for allowing fluid to flow through the second plunger portion to contact the deflection portion of the first plunger portion,
    wherein the deflection portion is movable from a generally concave, locked position, in which the central plug is received within and plugs the opening, to a convex, unlocked position, in which the central plug is separated from the opening to allow fluid flow through the opening.

2. Apparatus as in claim 1, wherein the cartridge or syringe defines a longitudinal axis, and wherein the deflection portion is configured to deflect in a distal direction along the longitudinal axis to move from the locked position to the unlocked position in response to pressure applied to a fluid in the cartridge or syringe proximal to the deflection portion.

3. Apparatus as in claim 1, wherein the cartridge or syringe includes a proximal end and a distal end, and wherein the deflection portion has a distal-facing concavity in the locked position and a proximal-facing concavity in the unlocked position.

4. Apparatus as in claim 1, further comprising at least one outer rib on an outer surface of the contact portion, wherein the deflection portion in the locked position biases the at least one outer rib against the cartridge or syringe.

5. Apparatus as in claim 1, wherein at least a portion of an outer surface of the plunger apparatus extends a greater horizontal distance across the cartridge or syringe in the locked position than in the unlocked position.

6. Apparatus as in claim 1, wherein the deflection portion and the contact portion comprise one piece of material.

7. Apparatus as in claim 1, wherein the at least one wall comprises multiple wall portions arrayed around an outer circumference of the second plunger portion, and wherein the at least one channel comprises multiple channels disposed between the multiple wall portions.

8. A system for temporarily separating two substances within a syringe and allowing for mixture of the two substances within the syringe, the system comprising:
    a syringe;
    a plunger configured to fit in the syringe, the plunger comprising:
        a first plunger portion comprising:
            an open end;
            a deflection portion opposite the open end and including an opening; and
            an outer, circumferential, contact portion configured to contact an inner surface of the syringe; and a second plunger portion configured for receipt within the first plunger portion and comprising:
   a central plug;
   at least one outer wall of the second plunger portion configured to contact an inner surface of the outer contact portion of the first plunger portion; and
   at least one channel for allowing fluid to flow through the second plunger portion to contact the deflection portion of the first plunger portion,
wherein the deflection portion is movable from a generally concave locked position, in which the central plug is received within and plugs the opening, to a convex, unlocked position, in which the central plug is separated from the opening to allow fluid flow through the opening.

9. A system as in claim 8, wherein the deflection portion is configured to move from the locked position to the unlocked position without moving through the syringe.

10. A system as in claim 8, wherein the syringe comprises a proximal end and a distal end, and wherein the deflection portion is configured to deflect in a distal direction, relative to the syringe, to move from the locked position to the unlocked position in response to pressure applied to a fluid in the syringe proximal to the deflection portion.

11. A system as in claim 8, further comprising a plunger driver configured to axially advance within the syringe, wherein the plunger driver is configured to urge the deflection portion from the locked position to the unlocked position.

12. A system as in claim 11, wherein the plunger driver is further configured to axially advance the contact portion and the deflection portion longitudinally through the syringe.

13. A system as in claim 8, wherein the at least one wall comprises multiple wall portions arrayed around an outer circumference of the second plunger portion, and wherein the at least one channel comprises multiple channels disposed between the multiple wall portions.

* * * * *